(12) United States Patent
Tymianski

(10) Patent No.: US 8,685,925 B2
(45) Date of Patent: Apr. 1, 2014

(54) METHOD AND COMPOSITIONS FOR TREATING STROKE WITH FEVER

(75) Inventor: Michael Tymianski, Toronto (CA)

(73) Assignee: Nono Inc., Ontario (CA)

( * ) Notice: Subject to any disclaimer, the term of this patent is extended or adjusted under 35 U.S.C. 154(b) by 928 days.

(21) Appl. No.: 12/307,581

(22) PCT Filed: Jul. 10, 2007

(86) PCT No.: PCT/US2007/015747
§ 371 (c)(1),
(2), (4) Date: Sep. 1, 2009

(87) PCT Pub. No.: WO2008/008348
PCT Pub. Date: Jan. 17, 2008

(65) Prior Publication Data
US 2012/0208764 A1     Aug. 16, 2012

Related U.S. Application Data

(60) Provisional application No. 60/830,189, filed on Jul. 11, 2006, provisional application No. 60/833,572, filed on Jul. 26, 2006.

(51) Int. Cl.
*A61K 38/00* (2006.01)
*A61K 38/18* (2006.01)
*A61K 38/10* (2006.01)
*A61K 38/16* (2006.01)
*A61K 38/08* (2006.01)
*A61K 38/06* (2006.01)
*A61K 38/07* (2006.01)

(52) U.S. Cl.
USPC ......... 514/17.7; 514/17.3; 514/19.1; 514/8.3; 514/21.4; 514/21.6; 514/21.9

(58) Field of Classification Search
None
See application file for complete search history.

(56) References Cited

U.S. PATENT DOCUMENTS

| 8,071,548 B2 * | 12/2011 | Tymianski | 514/17.7 |
| 8,080,518 B2 * | 12/2011 | Tymianski et al. | 514/1.1 |
| 2005/0059597 A1 * | 3/2005 | Tymianski | 514/12 |
| 2005/0164933 A1 | 7/2005 | Tymianski et al. | |

FOREIGN PATENT DOCUMENTS

| EP | 1 884 521 | 2/2006 |
| WO | WO 2004/045535 | 6/2004 |
| WO | WO 2005/061548 | 7/2005 |
| WO | WO 2008/109010 | 9/2008 |

OTHER PUBLICATIONS

Bach et al. (2008) "Modified peptides as potent inhibitors of the postsynaptic density-95/N-methyl-d-aspartate receptor interaction" J Med Chem 51:6450-6459.*
Moen and Wagstaff (2005) "Losartan: A review of its use in stroke risk reduction in patients with hypertension and left ventricular hypertrophy" Drugs 66(18):2657-2674.*
Neuhauser (2003) "Primary Prevention of Stroke" The Lancet 362 p. 2121.*
U.S. Appl. No. 13/377,523, filed Dec. 2011, Tymianski, Michael.*
U.S. Appl. No. 13/286,071, filed Oct. 2011, Tymianski, Michael.*
Lees 1997 "Cerestat and other NMDA antagonists in ischemic stroke" Neurology 49(Supp 4):S66-S69.*
Ginsberg and Busto 1998 "Combating hyperthermia in acute stroke: a significant clinical concern" Stroke 29:529-534.*
Noor et al. 2005 "Hyperthermia masks the neuroprotective effects of tissue plasminogen activator" Stroke 36:665-669.*
Memezawa et al. 1995 "Hyperthermia nullifies the ameliorating effect of dizocilpine maleate (MK-801) in focal cerebral ischemia" brain research 670:48-52.*
Castillo et al., "Timing for Fever-Related Brain Damage in Acute Ischemic Stroke," *Stroke*, 29:2455-2460, (1998).
EPO Third Party Observation concerning the patentability of application EP07796769.3 dated Aug. 6, 2012.
Kornau et al., "Domain Interaction between NMDA Receptor Subunits and the Postsynaptic Density Protein PSD-95," *Science*, 269(5231):1737-1740, (1995).
Lim et al., "Selectivity and Promiscuity of the First and Second PDZ Domains of PSD-95 and Synapse-associated Protein 102," *The Journal of Biological Chemistry*, 277(24): 21697-21711, (2002).
Aarts et al., "Treatment of Ischemic Brain Damage by Perturbing NMDA Receptor—PSD-95 Protein Interactions," Science, American Association for the Advancement of Science, Washington, DC; US LNKD-DOI:10.1126/Science.1072873, vol. 298, No. 5594, Oct. 25, 2002, pp. 846-850, XP002476284, ISSN: 0036-8075.
Liu Y et al., "Uncoupling NMDA Receptor-PSD-95 Protein Interactions Reduces Infraction in Focal Cerebral Ischemia in Rats," Abstracts of the Annual Meeting of the Society for Neuroscience, Society for neuroscience, Washington, DC, US Nov. 4, 2002, p. 245.3, XP009133058, ISSN: 0190-5295.
Chui H. et al., "PDZ Protein Interactions Underlying NMDA Receptor-Mediated Excitotoxicity and Neuroprotection by PSD-95 Inhibitors," Journal of Neuroscience, New York, NY, US LNKD-DOI:10. 1523/JNEUROSCI.1464-07.2007, vol. 27, No. 37 Sep. 12, 2007, pp. 9901-9915, XP002581414, ISSN: 0270-6474.
Supplementary European Search Report, mailed Aug. 18, 2010, EP Application No. 07796769.3, filed Jul. 10, 2007, 2 pages total.
"Evaluating Neuroprotection in Aneurysm Coiling Therapy (ENACT)," ClinicalTrials.gov, (2008). [Retrieved from the Internet Jul. 2, 2012: <URL: http://clinicaltrials.gov/ct2/show/NCT00728182>].
Alvarez-Sabin et al., "Effects of Admission Hyperglycemia on Stroke Outcome in Reperfused Tissue Plasminogen Activator—Treated Patients," Stroke, 34:1235-1240, (2003).

(Continued)

*Primary Examiner* — Jeffrey Stucker
*Assistant Examiner* — Adam M Weidner
(74) *Attorney, Agent, or Firm* — Alston & Bird LLP

(57) ABSTRACT

The invention provides methods of treating stroke and related conditions exacerbated by fever and/or hyperglycemia by administering peptides or peptidomimetics that inhibit binding of NMDAR 2B to PSD-95 to a patient.

16 Claims, 7 Drawing Sheets

(56) References Cited

OTHER PUBLICATIONS

Elsersy et al., "Effects of Isoflurane Versus Fentanyl—Nitrous Oxide Anesthesia on Long-term, Outcome from Severe Forebrain Ischemia in the Rat," Anesthesiology, 100:1160-1166, (2004).

Wang et al., "Influence of Admission Body Temperature on Stroke Mortality," *Stroke*, 31:404-409, (2000).

* cited by examiner

SEQUENCE LISTING

<160> NUMBER OF SEQ ID NOS: 24

<210> SEQ ID NO 1
<211> LENGTH: 3
<212> TYPE: PRT
<213> ORGANISM: Artificial
<220> FEATURE:
<223> OTHER INFORMATION: PL protein motif
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Val or Leu

<400> SEQUENCE: 1

Xaa Xaa Xaa
1

<210> SEQ ID NO 2

```
<211> LENGTH: 4
<212> TYPE: PRT
<213> ORGANISM: Artificial
<220> FEATURE:
<223> OTHER INFORMATION: PL protein motif
<220> FEATURE:
<221> NAME/KEY: MISC_FEATURE
<222> LOCATION: (1)..(1)
<223> OTHER INFORMATION: Xaa is Asp, Glu, Gln, or Asn
<220> FEATURE:
<221> NAME/KEY: MISC_FEATURE
<222> LOCATION: (2)..(2)
<223> OTHER INFORMATION: Xaa is Ser or Thr
<220> FEATURE:
<221> NAME/KEY: MISC_FEATURE
<222> LOCATION: (3)..(3)
<223> OTHER INFORMATION: Xaa is Asp, Glu, Gln, or Asn
<220> FEATURE:
<221> NAME/KEY: MISC_FEATURE
<222> LOCATION: (4)..(4)
<223> OTHER INFORMATION: Xaa is Val or Leu

<400> SEQUENCE: 2

Xaa Xaa Xaa Xaa
1

<210> SEQ ID NO 3
<211> LENGTH: 4
<212> TYPE: PRT
<213> ORGANISM: Artificial
<220> FEATURE:
<223> OTHER INFORMATION: PL protein motif

<400> SEQUENCE: 3

Glu Ser Asp Val
1

<210> SEQ ID NO 4
<211> LENGTH: 4
<212> TYPE: PRT
<213> ORGANISM: Artificial
<220> FEATURE:
<223> OTHER INFORMATION: PL protein motif

<400> SEQUENCE: 4

Glu Ser Glu Val
1

<210> SEQ ID NO 5
<211> LENGTH: 4
<212> TYPE: PRT
<213> ORGANISM: Artificial
<220> FEATURE:
<223> OTHER INFORMATION: PL protein motif

<400> SEQUENCE: 5

Glu Thr Asp Val
1

<210> SEQ ID NO 6
<211> LENGTH: 4
<212> TYPE: PRT
<213> ORGANISM: Artificial
<220> FEATURE:
<223> OTHER INFORMATION: PL protein motif

<400> SEQUENCE: 6

Glu Thr Glu Val
1
```

```
<210> SEQ ID NO 7
<211> LENGTH: 4
<212> TYPE: PRT
<213> ORGANISM: Artificial
<220> FEATURE:
<223> OTHER INFORMATION: PL protein motif

<400> SEQUENCE: 7

Asp Thr Asp Val
1

<210> SEQ ID NO 8
<211> LENGTH: 4
<212> TYPE: PRT
<213> ORGANISM: Artificial
<220> FEATURE:
<223> OTHER INFORMATION: PL protein motif

<400> SEQUENCE: 8

Asp Thr Glu Val
1

<210> SEQ ID NO 9
<211> LENGTH: 9
<212> TYPE: PRT
<213> ORGANISM: Artificial
<220> FEATURE:
<223> OTHER INFORMATION: PL protein motif

<400> SEQUENCE: 9

Lys Leu Ser Ser Ile Glu Ser Asp Val
1               5

<210> SEQ ID NO 10
<211> LENGTH: 9
<212> TYPE: PRT
<213> ORGANISM: Artificial
<220> FEATURE:
<223> OTHER INFORMATION: PL protein motif

<400> SEQUENCE: 10

Lys Leu Ser Ser Ile Glu Thr Asp Val
1               5

<210> SEQ ID NO 11
<211> LENGTH: 20
<212> TYPE: PRT
<213> ORGANISM: Human immunodeficiency virus
<220> FEATURE:
<223> OTHER INFORMATION: Tat Internalization Peptide

<400> SEQUENCE: 11

Tyr Gly Arg Lys Lys Arg Arg Gln Arg Arg Lys Leu Ser Ser Ile
1               5                   10                  15

Glu Thr Asp Val
            20

<210> SEQ ID NO 12
<211> LENGTH: 20
<212> TYPE: PRT
<213> ORGANISM: Human immunodeficiency virus
<220> FEATURE:
<223> OTHER INFORMATION: Tat Internalization Peptide

<400> SEQUENCE: 12

Tyr Gly Arg Lys Lys Arg Arg Gln Arg Arg Lys Leu Ser Ser Ile
1               5                   10                  15
```

Glu Ser Asp Val
            20

<210> SEQ ID NO 13
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 4
<212> TYPE: PRT
<213> ORGANISM: Artificial
<220> FEATURE:
<223> OTHER INFORMATION: NMDA C-terminal 4mer sequence

<400> SEQUENCE: 14

Ser Thr Val Val
1

<210> SEQ ID NO 15
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 15

Arg Arg Ala Ile Glu Arg Glu Glu Gly Gln Leu Gln Leu Cys Ser Arg
1               5                   10                  15

His Arg Glu Ser
            20

<210> SEQ ID NO 16
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 16

Thr Gln Gly Phe Pro Gly Pro Cys Thr Trp Arg Arg Ile Ser Ser Leu
1               5                   10                  15

Glu Ser Glu Val
            20

<210> SEQ ID NO 17
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 17

Phe Asn Gly Ser Ser Asn Gly His Val Tyr Glu Lys Leu Ser Ser Ile
1               5                   10                  15

Glu Ser Asp Val
            20

```
<210> SEQ ID NO 18
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 18

Ala Val Ser Arg Lys Thr Glu Leu Glu Glu Tyr Gln Arg Thr Ser Arg
1               5                   10                  15

Thr Cys Glu Ser
            20

<210> SEQ ID NO 19
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 19

Leu Asn Ser Cys Ser Asn Arg Arg Val Tyr Lys Lys Met Pro Ser Ile
1               5                   10                  15

Glu Ser Asp Val
            20

<210> SEQ ID NO 20
<211> LENGTH: 20
<212> TYPE: PRT
<213> ORGANISM: Artificial
<220> FEATURE:
<223> OTHER INFORMATION: NMDA C-terminal 20mer sequence

<400> SEQUENCE: 20

Gly Gly Asp Leu Gly Thr Arg Arg Gly Ser Ala His Phe Ser Ser Leu
1               5                   10                  15

Glu Ser Glu Val
            20

<210> SEQ ID NO 21
<211> LENGTH: 11
<212> TYPE: PRT
<213> ORGANISM: Human immunodeficiency virus

<400> SEQUENCE: 21

Tyr Gly Arg Lys Lys Arg Arg Gln Arg Arg Arg
1               5                   10

<210> SEQ ID NO 22
<211> LENGTH: 9
<212> TYPE: PRT
<213> ORGANISM: Artificial
<220> FEATURE:
<223> OTHER INFORMATION: PL protein motif

<400> SEQUENCE: 22

Lys Leu Ser Ser Ile Glu Ala Asp Ala
1               5

<210> SEQ ID NO 23
<211> LENGTH: 4
<212> TYPE: PRT
<213> ORGANISM: Artificial
<220> FEATURE:
<223> OTHER INFORMATION: NMDA C-terminal 4mer sequence
```

```
<400> SEQUENCE: 23

His Arg Glu Ser
1

<210> SEQ ID NO 24
<211> LENGTH: 4
<212> TYPE: PRT
<213> ORGANISM: Artificial
<220> FEATURE:
<223> OTHER INFORMATION: NMDA C-terminal 4mer sequence

<400> SEQUENCE: 24

Thr Cys Glu Ser
1
```

METHOD AND COMPOSITIONS FOR TREATING STROKE WITH FEVER

CROSS-REFERENCE TO RELATED APPLICATIONS

The present application is a nonprovisional of U.S. Ser. No. 60/830,189, filed Jul. 11, 2006 and U.S. Ser. No. 60/833,572, filed Jul. 26, 2007, both incorporated by reference in their entirety for all purposes.

REFERENCE TO A "SEQUENCE LISTING"

The sequence listing in file 397813_SEQLST.txt was created May 1, 2012 and is 5,900 bytes. This sequence listing is hereby incorporated by reference.

STATEMENT AS TO RIGHTS TO INVENTIONS MADE UNDER FEDERALLY SPONSORED RESEARCH OR DEVELOPMENT

This invention was made with Government support under NIH Grant Number NS048956. The Government may have certain rights in this invention.

BACKGROUND OF THE INVENTION

Stroke is predicted to affect more than 600,000 people in the United States a year. In a 1999 report, over 167,000 people died from strokes, with a total mortality of 278,000. In 1998, 3.6 billion was paid to just those Medicare beneficiaries that were discharged from short-stay hospitals, not including the long term care for >1,000,000 people that reportedly have functional limitations or difficulty with activities of daily living resulting from stroke (Heart and Stroke Statistical update, American Heart Association, 2002). No therapeutics has yet been approved to reduce brain damage resulting from stroke.

Stroke is characterized by neuronal cell death in areas of ischemia, brain hemorrhage anti/or trauma. Cell death is triggered by glutamate over-excitation of neurons, leading to increased intracellular $Ca^{2+}$ and increased nitric oxide due to an increase in nNOS (neuronal nitric oxide synthase) activity.

Glutamate is the main excitatory neurotransmitter in the central nervous system (CNS) and mediates neurotransmission across most excitatory synapses. Three classes of glutamate-gated ion channel receptors (N-methyl-D-aspartate (NMDA), alpha-amino-3-hydroxy-5-methylisoxazole-4-propionic acid (AMPA) and Kainate) transduce the postsynaptic signal. Of these, NMDA receptors (NMDAR) are responsible for a significant portion of the excitotoxicity of glutamate. NMDA receptors are complex having an NR1 subunit and one or more NR2 subunits (2A, 2B, 2C or 2D) (see, e.g., McDain, C. and Caner, M. (1994) *Physiol. Rev.* 74:723-760), and less commonly, an NR3 subunit (Chatterton et al. (2002) *Nature* 415:793-798). The NR1 subunits have been shown to bind glycine, whereas NR2 subunits bind glutamate. Both glycine and glutamate binding are required to open the ion channel and allow calcium entry into the cell. The four NR2 receptor subunits appear to determine the pharmacology and properties of NMDA receptors, with further contributions from alternative splicing of the NR1 subunit (Kornau et al. (1995) *Science* 269:1737-40). Whereas NR1 and NR2A subunits are ubiquitously expressed in the brain, NR2B expression is restricted to the forebrain, NR2C to the cerebellum, and NR2D is rare compared to the other types.

Because of the key role of NMDA receptors in the excitotoxicity response, they have been considered as targets for therapeutics. Compounds have been developed that target the ion channel (ketamine, phencyclidine, PCP, MK801, amantadine), the outer channel (magnesium), the glycine binding site on NR1 subunits, the glutamate binding site on NR2 subunits, and specific sites on NR2 subunits (Zinc—NR2A; Ifenprodil, Traxoprodil—NR2B). Among these, the non-selective antagonists of NMDA receptor have been the most neuroprotective agents in animal models of stroke. However, clinical trials with these drugs in stroke and traumatic brain injury have so far failed, generally as a result of severe side effects such as hallucination and even coma. Other criticisms of past animal stroke studies include that the efficacy of many neuroprotectants was determined in mild ischemia models (ischemia-reperfusion instead of permanent ischemia), and under conditions of food deprivation, which can not adequately mimic the more severe human situation. Also, most drugs were administered pre-ischemia whereas human trials necessitate a post-treatment paradigm (Gladstone et al., 2002; STAIR Committee, 1999).

Another key difference between human stroke and experimental ischemia is that some stroke victims also suffer from aggravating premorbid or comormid conditions or stroke-related complications. Prominent among these is hyperglycemia (Alvarez-Sabin, 2003), especially in diabetic patients (Paolino, 2005), but also in non-diabetics (Alvarez-Sabin, 2003). However, hyperglycemia is actively avoided in laboratory stroke studies as it is known to exacerbate cerebral infarction (Li, 1997, 1998, 2000, 2001; Farrokhnia, 2005), and experimental animals are routinely fasted to minimize intra-ischemic blood glucose elevations (Elsersy, 2004; Horiguchi, 2003; Belayev, 2005a). Fever is another complication that afflicts some stroke victims, and is an independent predictor of poor outcome (Azzimondi, 1995; Reith, 1996; Boysen, 2001; Ginsberg, 1998). Hyperthermia has long been known to exacerbate both global and focal experimental ischemic injury (Busto, 1987b, 1989a, 1989b; Ginsberg, 1992; Morikawa, 1992; Chen, 1993; Minamisawa, 1990a, 1990b, 1990c; Chen, 1991) and, precisely for this reason, has been strongly avoided in studies of neuroprotective drugs.

The present inventor has reported that postsynaptic density-95 protein (PSD-95) couples NMDARs to pathways mediating excitotoxicity and ischemic brain damage (Aarts et al., Science 298, 846-850 (2002)). This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and reduced cerebral infarction volume in rats subjected to transient focal cerebral ischemia. The analysis was performed under conditions of transient ischemia and prior fasting to avoid exacerbating fever and hyperglycemia.

SUMMARY OF THE CLAIMED INVENTION

The invention provides the use of a peptide having an amino acid sequence comprising T/SXV/L (SEQ ID NO:1) or a peptidomimetic thereof for manufacture of a medicament for treatment of the damaging effect of stroke or other injury to the CNS exacerbated by fever or hyperglycemia.

The invention further provides a method of screening a compound that inhibits binding of PSD-95 to NDMAR, comprising administering the compound to a animal having ischemia exacerbated by hyperthermia and/or hyperglycemia; and determining whether the compound reduces infarction volume resulting from the ischemia relative to a control animal not treated with the compound.

The invention further provides a method for reducing the damaging effect of stroke in a patient having stroke or other injury to the CNS exacerbated by fever or hyperglycemia comprising administering an effective amount of a peptide having an amino acid sequence comprising T/S-[X]-V/L (SEQ ID NO:1), or peptidomimetic thereof, and thereby reducing the damaging effect of the stroke or other injury.

The invention further provides for the use of a peptide having an amino acid sequence comprising T/SXV/L (SEQ ID NO:1) or a peptidomimetic thereof in the manufacture of a medicament for treating the damaging effect of stroke or other CNS injury in a patient having fever or hyperglycemia.

The invention further provides for the use of a peptide having an amino acid sequence comprising T/SXV/L (SEQ ID NO:1) or a peptidomimetic thereof in the manufacture of a medicament for the prophylactic treatment of the damaging effect of stroke or other CNS injury in a patient with fever or hyperglycemia.

DETAILED DESCRIPTION OF THE INVENTION

I. Definitions

Figure 1:
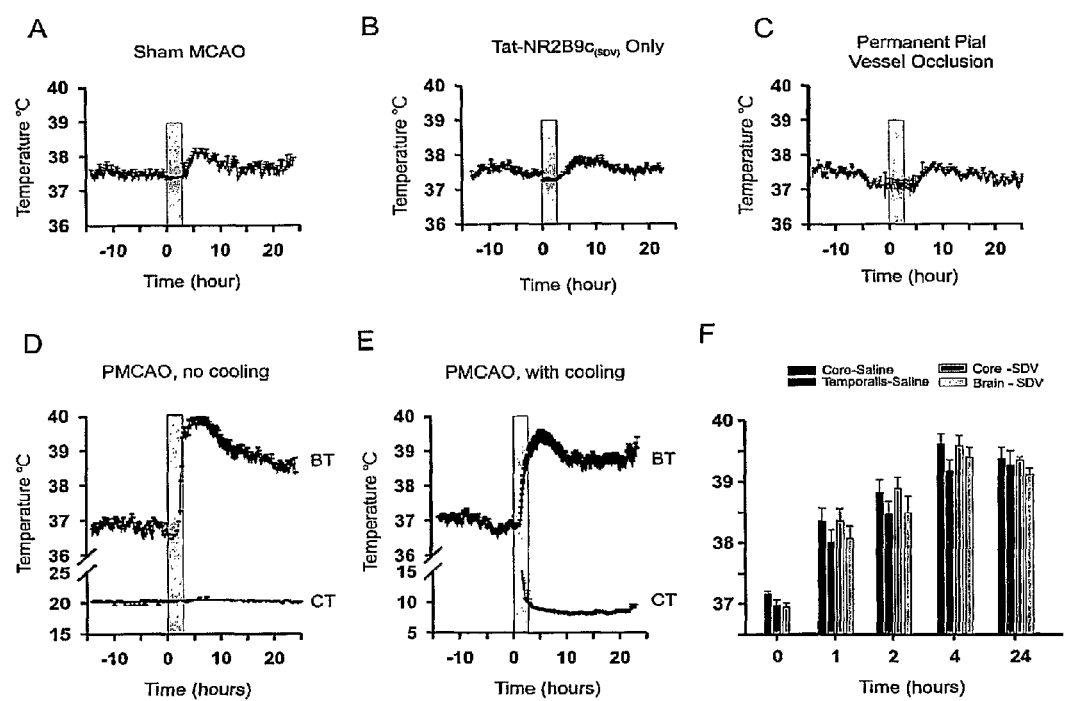
FIG. 1. Effects of ischemia models on core temperature. Animals in A-E were implanted with intra-peritoneal telemetric temperature probes and exposed to the indicated conditions. Gray bars indicate duration of animal surgery. A. Sham procedure (n=4). B. Sham procedure with administration of Tat-NR2B9c$_{(SDV)}$ (n=6). C. Pial vessel occlusion (n=5). D. Permanent MCAO without cage cooling. (n=8). E. Permanent MCAO with cage cooling using a feedback system (n=8). CT: Core temperature. Cage: Cage temperature. Symbols in A-E indicate the means+SE of the indicated number of animals. F. Effects of the indicated conditions on temporalis muscle, core, and brain temperature at the indicated times post pMCAO. Core-Saline: animals treated with saline 1 h post pMCAO (n=6). Temporalis-Saline: Concurrent temporalis muscle temperatures from saline treated animals. Core-SDV: animals treated with Tat-NR2B9c$_{(SDV)}$ 1 h post pMCAO (n=6). Brain-SDV: Concurrent direct brain temperature measurements from NR2B9c$_{(SDV)}$-treated animals.

A "fusion polypeptide" refers to a composite polypeptide, i.e., a single contiguous amino acid sequence, made up of two (or more) distinct, heterologous polypeptides which are not normally fused together in a single amino acid sequence.

The term "PDZ domain" refers to a modular protein domain of about 90 amino acids, characterized by significant sequence identity (e.g., at least 60%) to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA. The term thus includes the various subunit forms described in the Background Section. Such receptors can be human or non- (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

A "peptidomimetic" and refers to a synthetic chemical compound which has substantially the same structural and/or functional characteristics of a peptide of the invention. The peptidomimetic can contain entirely synthetic, non-natural analogues of amino acids, or, is a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Statistically significant refers to a p-value that is <0.05, preferably <0.01 and most preferably <0.001.

II. General

The invention provides peptides and peptidomimetics useful for reducing damaging effects of stroke and other neurological conditions exacerbated by fever and/or hyperglycemia. The subsets of patients afflicted with one or both of these exacerbating factors have a significantly poorer outcome compared with patients in which these factors are present. The invention is based in part on results described in the examples in which certain peptides were found to reduce infarction volume in a rat model of permanent ischemia notwithstanding severe hyperthermia (≥39° C.) and lack of prior fasting. Surprisingly, subjects with stroke and fever or hyperglycemia can be treated as effectively as subjects not suffering from such comorbid complications. Peptides used in such methods have an amino acid sequence including or based on the PL motif of NMDAR 2B receptor (i.e., PL peptides). Although an understanding of mechanism is not required for practice of the invention, it is believed that such peptides act at least in part by inhibiting interaction between NMDARs with postsynaptic density 95 protein (i.e., PSD-95 inhibitors). The peptides may also inhibit interactions between PSD-95 and nNOS. Unlike glutamate antagonists that have previously failed clinical trials, such peptides can disrupt neurotoxic signaling during ischemic without incurring the negative consequences of loss of NMDAR function.

III. Peptides and Peptidomimetics

Peptides and peptidomimetics useful in the invention inhibit interaction between domain 2 of postsynaptic density-95 protein (PSD-95 d2) containing a PDZ domain (Stathakism, Genomics 44(1):71-82 (1997)) and the C-terminus of NR2B subunit of the neuronal N-methyl-D-aspartate receptor (NMDAR) containing a PL motif (Mandich et al., Genomics 22, 216-8 (1994)). Such peptides include or are based on a PL motif from the C-terminus of this subunit and have an amino acid sequence comprising [S/T]-X-[V/L] (SEQ ID NO.: 1). This sequence preferably occurs at the C-terminus of the peptides of the invention. Preferred peptides have an amino acid sequence comprising [E/D/N/Q]-[S/T]-[D/E/Q/N]-[V/L] (SEQ ID NO.: 2) at their C-terminus. Exemplary peptides comprise: ESDV (SEQ ID NO.: 3), ESEV (SEQ ID NO.: 4), ETDV (SEQ ID NO.: 5), ETEV (SEQ ID NO.: 6), DTDV (SEQ ID NO.: 7), and DTEV (SEQ ID NO.: 8). Two particularly preferred peptides are KLSSIESDV (SEQ ID NO.: 9), and KLSSIETDV (SEQ ID NO.: 10).

Any of the peptides of the invention can be linked, preferably at their N-terminus, to an internalization peptide that facilitates translocation through the plasma membrane of a cell. For example, the HIV TAT internalization peptide YGRKKRRQRRR can be used. An internalization peptide derived from Antennapedia can also be used (see Bonfanti, Cancer Res. 57, 1442-6 (1997)). Two preferred peptides including the HIV Tat internalization peptide are YGRKKRRQRRRKLSSIETDV (SEQ ID NO.: 11, Tat-NR2B9c$_{(TDV)}$), and YGRKKRRQRRRKLSSIESDV (SEQ ID NO.: 12, Tat-NR2B9c$_{(SDV)}$).

Peptides of the invention without an internalization peptide usually have 3-25 amino acids, Peptide lengths (also without an internalization peptide) of 5-10 amino acids, and particularly 9 amino acids are preferred.

Appropriate pharmacological activity of peptides or peptidomimetics can be confirmed, if desired, using the animal model described in the Examples. Optionally, peptides or peptidomimetics can also be screened for capacity to inhibit interactions between PSD-95 and NDMAR 2B using assays described in e.g., US 20050059597, which is herein incorporated by reference. Useful peptides typically have IC50 values of less than 50 uM, 25 μM, 10 uM, 0.1 μM or 0.01 μM in such an assay. Preferred peptides typically have an IC50 value of between 0.001-1 μM, and more preferably 0.05-0.5 or 0.05 to 0.1 μM Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Peptides of the invention, optionally fused to internalization domains, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

IV. Stroke and Related Conditions

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

Several other neurological conditions can also result in neurological death through NDMAR-mediated excitotoxicity. These conditions include epilepsy, hypoxia, traumatic injury to the CNS not associated with stroke such as traumatic brain injury and spinal cord injury, Alzheimer's disease and Parkinson's diseaseV. Conditions Exacerbating Stroke A subset of stroke patients have exacerbating fever and/or hyperglycemia, which are comorbid conditions, that in the absence of treatment by the present methods predispose patients to a poorer outcome than is the case for all stroke patients, particularly stroke patients lacking such an exacerbating comorbidity.

Fever (also known as pyrexia) means an increase in internal body temperature to a level at least 0.5° C. above normal (37° C., 98.6° F.). In some patients the fever is at least 38, 39 or 40° C. Fever is related to hyperthermia, which is an acute condition resulting from an increase in body temperature over the body's normal thermoregulatory set-point (due to excessive heat production or insufficient thermoregulation, or an altered thermoregulatory set point or any combination thereof). Fever exacerbates stroke by promoting infarct formation.

Fever, as an exacerbating comorbid condition with stroke, can result from several circumstances. Some patients have an infection before the stroke occurs resulting in fever at the time of the stroke, at the time of treatment, (usually 1-6 hr after the stroke) and usually persisting at least 24 hours after treatment. Other patients do not have fever at the onset of stroke, but develop fever because the stroke affects an area of the brain that controls temperature of the patient. Such a fever can develop between onset of the stroke and initiation of treatment, and can persist for at least 24 hours after treatment. Such a fever can also develop after treatment has begun and persist for a period of at least 24 hours after initiation of treatment. This type of spontaneous fever has been associated with large strokes in humans (Azzimondi et al., 1995; Reith et al., 1996; Ginsberg and Busto, 1998; Boysen and Christensen, 2001). Other patients have fever as a result of being exposed to high temperatures at the time of onset of stroke. Such fever typically persists through initiation of treatment of the patient, but may diminish thereafter.

Hyperglycemia or high blood sugar is a condition in which an excessive amount of glucose circulates in the blood plasma. Blood glucose levels can be measured in either milligrams per deciliter (mg/dL) or in millimoles per liter (mmol/L). In general, normal fasting blood glucose levels range from about 80 to 120 mg/dL or 4 to 7 mmol/L. Fasting blood glucose levels above about 126 mg/dL or 7 mmol/L are hyperglycemic Although the mechanism by which hyperglycemia exacerbates stroke is controversial, one mechanism is the promotion of tissue acidosis (lowered pH), and/or the activation many intracellular responses such as the activities of protein kinases and protein phosphorylation, intracellular calcium metabolism, and hormone metabolism including glucocorticoids.]

Hyperglycemia as an exacerbating comorbidity with stroke can also result from several circumstances. One circumstance is concurrent presence of diabetes, both type I and II. Although glycemic levels can be controlled to some extent by administration of insulin, diabetes patients are particularly vulnerable to swings in glycemic levels. Hyperglycemia can also be the result of eating a large meal, particularly one rich in simple carbohydrates, before onset of a stroke.

VI. Methods of Treatment

The peptides or peptidomimetics described above are used to treat patients with stroke exacerbated by fever and/or hyperglycemia, as described above. Treatment is usually initiated as soon as possible after initiation of the stroke. Occasionally, treatment can be initiated at or before onset of stroke in patients known to be at high risk. Risk factors include hypertension, diabetes, family history, smoking, previous stroke, and undergoing surgery. Usually, treatment is first administered within one to six hours after initiation of stroke. Optionally, the temperature of the patient and/or blood glycemic level of the patient is measured before commencing treatment to determine presence or absence of fever and/or hyperglycemia. Presence of diabetes or other metabolic condition disposing the subject to hyperglycemia can also be determined. Optionally, the temperature and blood glycemic level of the patient are monitored at several intervals or at least daily after receiving treatment. Often a single dose of peptide or peptidomimetic of the invention is sufficient. However, multiple doses can also be administered at intervals of 6-24 hr.

The response of the patient to the treatment can be monitored by determining infarction volume before and at various times after treatment Early ischemia is detectable using MRI diffusion imaging. Combinations of MRI protocols, including perfusion imaging, can be used to determine tissue at risk and predict infarction volume. The methods preferably achieve a reduction in infarction volume of at least 10, 15, 20, 25, 30, 35, 40, or 50% relative to the mean infarction volume in a population of comparable patients not receiving treatment by the methods of the invention. The response of the patient can also be measured from a disability index determined one day to one week after initiating treatment. The patient preferably shows an improvement (i.e., less disability) in disability index of at least 4, 10, 15, 20, 25, 30, 35, 40, or 50% relative to the mean disability index in a population of comparable patients not receiving treatment by the methods of the invention The patient preferably scores a zero or one on the Rankin stroke index or over 75 on the Barthel index.

VII. Pharmaceutical Compositions, Dosages and Routes of Administration

The peptides and peptidomimetics of the invention can be administered in the form of a pharmaceutical composition. Pharmaceutical compositions are manufactured under GMP conditions. Pharmaceutical compositions can be provided in unit dosage form (i.e., the dosage for a single administration) containing any of the dosages indicated above. Pharmaceutical compositions can be manufactured by means of conventional mixing, dissolving, granulating, dragee-making, levigating, emulsifying, encapsulating, entrapping or lyophilizing processes. In particularly, lypholyized peptides or peptidomimetics of the invention can be used in the formulations and compositions described below.

Pharmaceutical compositions can be formulated in conventional manner using one or more physiologically acceptable carriers, diluents, excipients or auxiliaries that facilitate processing of peptides or peptidomimetics into preparations which can be used pharmaceutically. Proper formulation is dependent on the route of administration chosen.

Administration can be parenteral, intravenous, oral, subcutaneous, intraarterial, intracranial, intrathecal, intraperitoneal, topical, intranasal or intramuscular. Intravenous administration is preferred.

Pharmaceutical compositions for parenteral administration are preferably sterile and substantially isotonic. For injection, peptides or peptidomimetics can be formulated in aqueous solutions, preferably in physiologically compatible buffers such as Hanks's solution, Ringer's solution, or physiological saline or acetate buffer (to reduce discomfort at the site of injection). The solution can contain formulatory agents such as suspending, stabilizing and/or dispersing agents.

Alternatively the peptides or peptidomimetics can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the compounds can be formulated by combining the peptides or peptidomimetics with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver peptides and peptidomimetics. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the peptides or peptidomimetics for a few weeks up to over 100 days. Depending on the chemical nature and the biological stability of the therapeutic reagent, additional strategies for protein stabilization can be employed.

As the peptides or peptidomimetics of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The peptides or peptidomimetics of the invention are used in an amount effective to achieve the intended purpose (e.g., reduction of damage effect of the damaging stroke and related conditions). A therapeutically effective amount means an amount of peptide or peptidomimetic sufficient to significantly reduce the damage resulting from stroke in a population of patients (or animal models) treated with the peptides or peptidomimetics of the invention relative to the damage in a control population of stroke patients (or animal models) not treated with the peptides or peptidomimetics of the invention. The amount is also considered therapeutically effective if an individual treated patient achieves an outcome more favorable than the mean outcome (determined by infarction volume or disability index) in a control population of comparable patients not treated by methods of the invention. The amount is also considered therapeutically effective if an individual treated patient shows a disability of two or less on the Rankin scale and 75 or more on the Barthel scale. A dosage is also considered therapeutically effective if a population of treated patients shows a significantly improved (i.e., less disability) distribution of scores on a disability scale than a comparable untreated population, see Lees et at 1., N Engl J Med 2006; 354:588-600A therapeutically effective regime means a combination of a therapeutically effective dose and a frequency of administration needed to achieve the intended purpose as described above. Usually a single administration is sufficient.

Preferred dosage ranges include 0.001 to 20 µmol peptide or peptidomimetic per kg patient body weight, optionally 0.03 to 3 µmol peptide or peptidomimetic per kg patient body weight to µmol peptide or peptidomimetic per kg patient body weight within 6 hours of stroke. In some methods, 0.1-20 µmol peptide or peptidomimetic per kg patient body weight within 6 hours are administered. In some methods, 0.1-10 µmol peptide or peptidomimetic per kg patient body weight is administered within 6 hours, more preferably about 0.3 µmol peptide or peptidomimetic per kg patient body weight within 6 hours. In other instances, the dosages range is from 0.005 to 0.5 µmol peptide or peptidomimetic per kg patient body weight. Dosage per kg body weight can be converted from rats to humans by dividing by 6.2 to compensate for different surface area to mass ratios. Dosages can be converted from units of moles to grams by multiplying by the molar weight of a peptide. Suitable dosages of peptides or peptidomimetics for use in humans can include 0.001 to 5 mg/kg patient body weight, or more preferably 0.005 to 1 mg/kg patient body weight or 0.05 to 1 mg/kg, or 0.09 to 0.9 mg/kg. In absolute weight for a 75 kg patient, these dosages translate to 0.075-375 mg, 0.375 to 75 mg or 3.75 mg to 75 mg or 6.7 to 67 mg. Rounded to encompass variations in e.g., patient weight, the dosage is usually within 0.05 to 500 mg, preferably 0.1 to 100 mg, 0.5 to 50 mg, or 1-20 mg.

The amount of peptide or peptidomimetic administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the present peptides or peptidomimetics can provide therapeutic benefit without causing substantial toxicity. Toxicity of the peptides or peptidomimetics can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Peptides or peptidomimetics exhibiting high therapeutic indices are preferred (see, e.g., Fingi et al., 1975, In: *The Pharmacological Basis of Therapeutics*, Ch. 1, p. 1).

VIII. Screening Methods

The invention further provides methods of screening peptides, peptidomimetics and other compounds for activity useful in reducing damaging effects of stroke. The methods are particularly useful for screening compounds known to inhibit interactions between PSD-95 and NMDRA 2B. Compounds are administered to an animal model of stroke, in which the animal has fever and/or hyperglycemia at the time of administering the compound. Fever can be induced by the ischemic event. For example, the rats subject to permanent focal ischemia described in the Examples spontaneously develop fever probably due to the ischemia affecting an area of the brain affecting brain controlling temperature regulation [Experimental animals can also be caused to have a fever by the introduction of pyrogenic substances such as bacterial products (endotoxins) that cause them to have a fever, or by increasing the ambient temperature using heating lamps, heating blankets, or other heating devices, to a degree that exceeds the animal's ability to thermoregulate through usual physiological mechanisms such as sweating or, vasodilation The animals can be subject to hyperglycemia simply by feeding them within 6 or 12 hours of initiating ischemia. After administering compounds to the animals, infarction volume and/or disability index are determined. Infarction volumes are usually determined 24 hr post treatment but can be determined at a later time such as 3, 7, 14 or 60 days. Disability index can be monitored over time, e.g., at 2 hr post treatment, 24 hr post treatment, one week and one month post treatment. Compounds showing a statistically significant reduction in infarction volume and/or disability index relative to control animals not treated with the compounds are identified as having activity useful for practicing the methods of the invention.

Compounds suitable for screening in the methods include peptides, peptidomimetics and small molecules (i.e., less than 500 Da) known to inhibit interactions of PSD-95 and NDMAR 2B. Other peptides, peptidomimetics and small molecules known to inhibit interactions between other pairs of NDMAR and PDZ domain proteins shown in Table A can also be screened.

TABLE A

NMDA RECEPTORS WITH PL SEQUENCES

| Name | GI# | C-terminal 20mer sequence | C-terminal 4mer sequence | PL? | internal PL ID |
|---|---|---|---|---|---|
| NMDAR1 | 307302 | HPTDITGPLNLSDPSVSTVV (SEQ ID NO: 13) | STVV (SEQ ID NO: 14) | X | AA216 |
| NMDAR1-1 | 292282 | HPTDITGPLNLSDPSVSTVV (SEQ ID NO: 13) | STVV (SEQ ID NO: 14) | X | AA216 |
| NMDAR1-4 | 472845 | HPTDITGPLNLSDPSVSTVV (SEQ ID NO: 13) | STVV (SEQ ID NO: 14) | X | AA216 |
| NMDAR1-3b | 2343286 | HPTDITGPLNLSDPSVSTVV (SEQ ID NO: 13) | STVV (SEQ ID NO: 14) | X | AA216 |
| NMDAR1-4b | 2343288 | HPTDITGPLNLSDPSVSTVV (SEQ ID NO: 13) | STVV (SEQ ID NO: 14) | X | AA216 |
| NMDAR1-2 | 11038634 | RRAIEREEGQLQLCSRHRES (SEQ ID NO: 15) | HRES (SEQ ID NO: 23) | | |
| NMDAR1-3 | 11038636 | RRAIEREEGQLQLCSRHRES (SEQ ID NO: 15) | HRES (SEQ ID NO: 23) | | |
| NMDAR2C | 6006004 | TQGFPGPCTWRRISSLESEV (SEQ ID NO: 16) | ESEV (SEQ ID NO: 4) | X | AA180 |
| NMDAR3 | 560546 | FNGSSNGHVYEKLSSIESDV (SEQ ID NO: 17) | ESDV (SEQ ID NO: 3) | X | AA34.1 |
| NMDAR3A | 17530176 | AVSRKTELEEYQRTSRTCES (SEQ ID NO: 18) | TCES (SEQ ID NO: 24) | | |
| NMDAR2B | 4099612 | FNGSSNGHVYEKLSSIESDV (SEQ ID NO: 17) | ESDV (SEQ ID NO: 3) | X | |
| NMDAR2A | 558748 | LNSCSNRRVYKKMPSIESDV (SEQ ID NO: 19) | ESDV (SEQ ID NO: 3) | X | AA34.2 |
| NMDAR2D | 4504130 | GGDLGTRRGSAHFSSLESEV (SEQ ID NO: 20) | ESEV (SEQ ID NO: 4) | X | |

Compounds to be screened can be both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Compounds can be prepared from diversity libraries, such as random or combinatorial peptide or non-peptide libraries. Libraries include chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science*, 249:404-406; Christian, R. B., et al., 1992, *J. Mol. Biol.* 227:711-718); Lenstra, 1992, *J. Immunol. Meth.* 152:149-157; Kay et al., 1993, *Gene* 128:59-65; WO 94/18318 dated Aug. 18, 1994. In vitro translation-based libraries include those described in WO 91/05058; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

EXAMPLES

Materials and Methods

PSD-95 Inhibitors

Synthetic peptides (Advanced Protein Technology Centre, Hospital for Sick Kids, Toronto, Ontario or BACHEM California), were designed to inhibit the interactions of NMDARs with the submembrane scaffolding protein PSD-95PSD-95 binds NMDAR NR2 subunits as well as nNOS through its second PDZ domain (pDZ2; reviewed in Hung, 2002), thus keeping nNOS in a close functional association with NMDARs (Brenman, 1996; Brenman, 1997). The interaction between NMDAR NR2B subunits and the PDZ2 domain of PSD-95 depends on a conserved C-terminus T/SXV motifofNR2B (Kornau, 1995). This interaction can be disrupted by the intracellular introduction of exogenous proteins that contain a 9 residue peptide sequence containing the SXV PDZ-domain binding motif of NR2B (KLSSIESDV (SEQ ID NO.:9); termed NR2B9c$_{(SDV)}$) (Aarts, 2002). Here, an additional sequence was synthesized containing the TXV motif (KLSSIETDV (SEQ ID NO.:10); termed NR2B9c$_{(TDV)}$), which also interacts with the PDZ2 domain of PSD-9S (Kornau, 1995). These peptides associate with PSD-9S through Type-I PDZ domain interactions (Reviewed in Aarts, 2004). A control peptide was also synthesized, in which the residues in positions 0 and −2 of the C-terminal T/SXV motif were mutated to alanines (KLSSIEADA (SEQ ID NO.: 22); termed NR2B$_{(ADA)}$), rendering this peptide incapable of binding PSD-95 (Kornau, 1995; Aarts, 2002).

NR2B9c$_{(SDV)}$, NR2B9c$_{(TDV)}$ or NR2B$_{(ADA)}$ on their own are not anticipated to enter cells and therefore, each peptide was fused to a corresponding cell-membrane protein transduction domain (PTD) of the HIV-1-Tat protein (YGRKKRRQRRR (SEQ ID NO.: 21); Tat) to obtain the 20 amino acid peptides Tat-NR2B9c$_{(SDV)}$, Tat-NR2B9c$_{(TDV)}$ and Tat-NR2B$_{(ADA)}$. The Tat PTD transduces cell membranes in a rapid, dose-dependent manner (Schwarze, 1999). This approach was previously used to successfully introduce small peptides and fusion proteins into CNS neurons in-vitro and in-vivo (Aarts, 2002; Arundine, 2004), and many others by now have shown that protein transduction can be used to deliver systemically administered proteins into the brain during and after stroke (Asoh, 2002; Borsello, 2003; Cao, 2002; Denicourt, 2003; Dietz, 2002; Eum, 2004; Kilic, 2002, 2003; Kim, 2005).

The peptides were prepared daily from lyophilized powder by dissolving them in normal saline to the final desired concentration. They were administered intravenously via a slow (4-5 min) injection by individuals blinded to the treatment group.

Experiments were performed in male adult Sprague-Dawley rats weighing 250-300 g (Charles River Laboratory, Canada). All procedures conformed to guidelines established by the Canadian Council on Animal Care and with the approval of the University Health Network animal care committee. All animals were housed in groups of 1-2 animals in cages with free access to food and water and in rooms having an ambient temperature of 20±1° C. and 12:12 hr light/dark cycle.

Surgical Preparation

Each animal was weighed and then anesthesia was induced. For the permanent pial vessel occlusion model, rats were anesthetized with ketamine (100 mg/kg), acepromazine (2 mg/kg), and xylazine (50 mg/kg), supplemented with one third the initial dose as required. For the two permanent middle cerebral artery occlusion (pMCAO) studies, anesthesia was induced with 3.5% halothane in a mixture of nitrous oxide and oxygen (Vol. 2:1) and maintained with 0.8% halothane in the mixture. Rats were endotracheally intubated and mechanically ventilated (60 strokes/min, tidal volume of 30-35 ml). A rectal temperature probe was inserted. Polyethylene catheters (PE-50) were introduced into the left femoral artery and vein for blood pressure recording, blood sampling, and drug injection. Mean arterial blood pressure was measured with the use of an indwelling femoral arterial catheter connected to a pressure transducer and was recorded continuously. Serial measurements were made of arterial blood gases, pH, and blood glucose.

Core, Brain and Temporalis Temperature Measurements and Temperature Control

A day prior to undergoing ischemia, the animals were implanted with intraperitoneal transmitters (E-Mitter; Mini Mitter/Respironics, Oregon, USA) permitting core temperature (CT) and activity monitoring. Monitoring was performed continuously from 20 hours before, to 24 hours after, the pMCAO (Mini-Mitter VitalView telemetric monitoring software; Mini Mitter/Respironics, Oregon, USA). During the animal surgery the animals were away from the telemetric receivers, so CT was measured with a rectal probe and maintained at 36.5° C. to 37.5° C. using a heating lamp or homeothermic blanket. To measure brain temperatures following pMCAO, the right skull was exposed and a 1 mm diameter hole drilled at the following stereotactic coordinates: from bregma, AP 3.3 mm, ML 4.0 mm, DV 3.0 mm. A blunt-tip 19 gauge metal cannula (10 mm length) was inserted to a depth of 5 mm and fixed in place with dental glue. Brain temperature was recoded at 0, 1, 2, 4 and 24 h using a small thermocouple probe inserted into the metal cannula. Temporalis muscle temperatures were measured with the same thermocouple probe inserted into the muscle through an 18 gauge needle. Cage temperatures were continuously recorded using an external temperature probe and software (Tektronix WaveStar software; Tektronix, Texas, USA) running on a digital oscilloscope and a separate computer. In some experiments, cage temperature was continuously adjusted based on the animal's CT using a custom-built feedback control setup that drove a Peltier-based cooling device (Igloo KoolMate 18; Texas, USA). The cooling device was automatically activated whenever the animal's CT exceeded a threshold of 37.1° C.

Permanent Distal Middle Cerebral Artery Pial Vessel Occlusion

Figure 2:
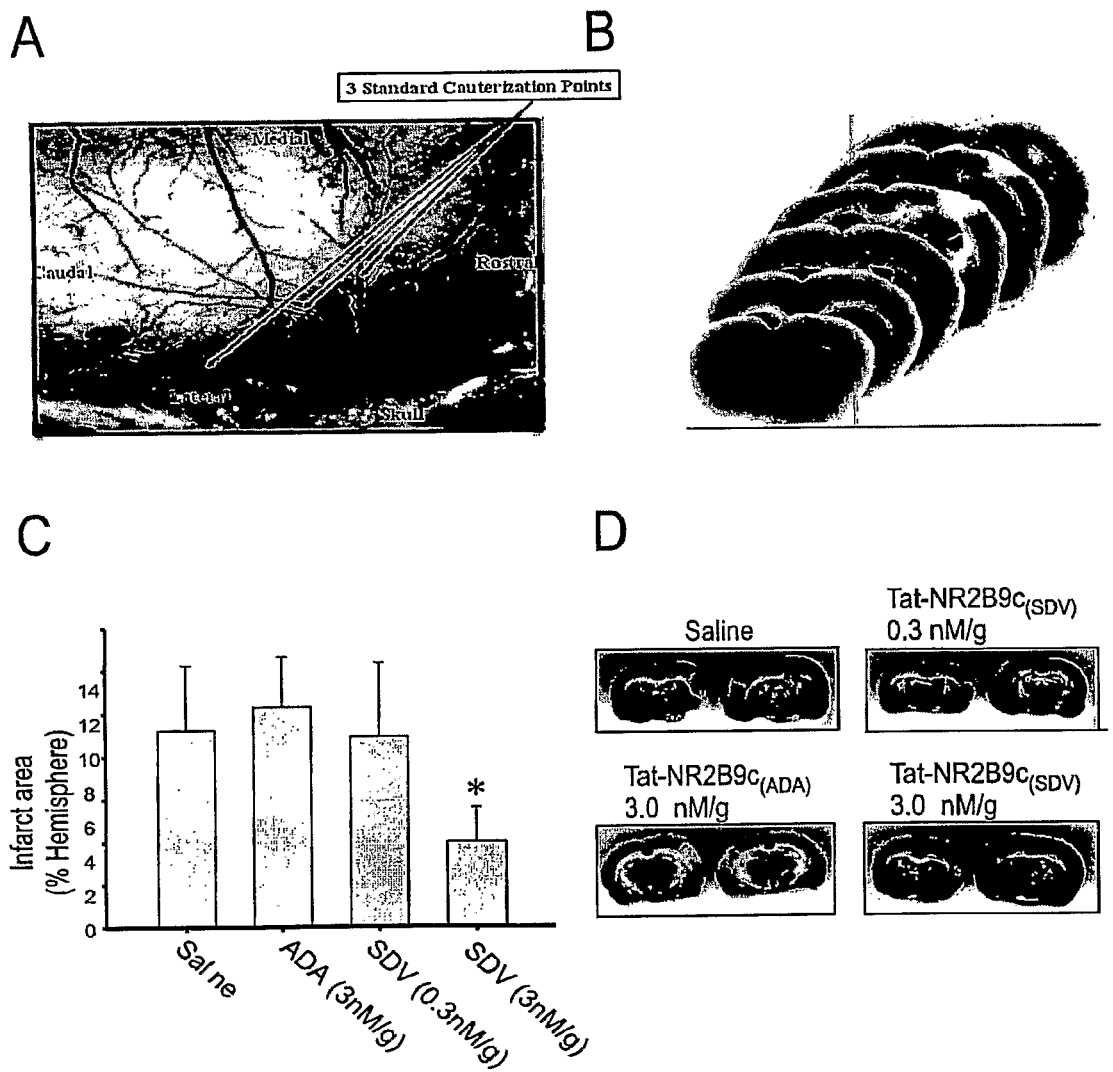
FIG. 2. Effect of Tat-NR2B9c$_{(SDV)}$ post-treatment in the permanent pial vessel occlusion model. A. The three sites of pial vessel occlusion. B. Resulting typical infarct in TTC stained brain. C. Effect of the indicated drug and drug concentration on infarct size. Number of animals per group is provided in Table 1. Asterisk: significantly different from both saline and ADA controls (ANOVA, p<0.05). ADA: Tat-NR2B9c$_{(ADA)}$. SDV: Tat-NR2B9c$_{(SDV)}$. D. Representative infarcts in TTC-stained coronal sections from each group.
Figure 3:
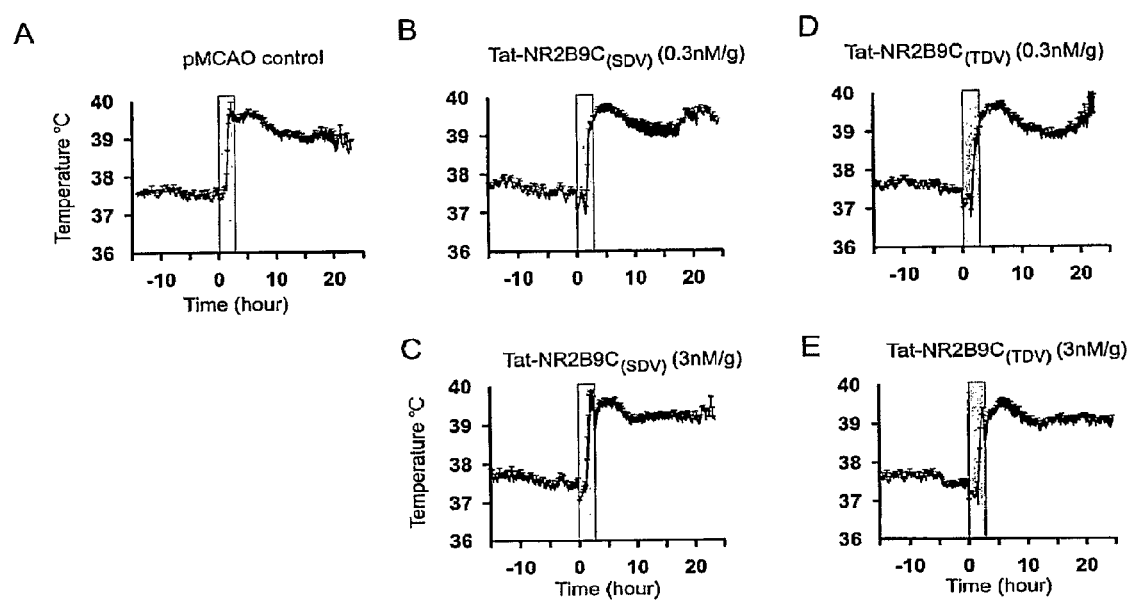
FIG. 3. PSD-95 inhibitors do not affect the hyperthermic response following pMCAO. A-E: Core temperatures before, during (gray bars) and following pMCAO surgery in animals treated with the indicated PSD-95 inhibitor at the indicated dose. N=8 for each group.

This was carried out as described elsewhere (Forder, 2005). In Brief, the right ECA was cannulated with PE 10 polyethylene tubing. The skull was exposed via a midline incision, and a 6- to 8-mm cranial window was made over the right somatosensory cortex (2 mm caudal and 5 mm lateral to bregma). The pial arteries were visualized by injecting small boluses (10-20 μL) of the vital dye patent blue violet (10 mMol/L; Sigma) in normal saline, into the ECA (FIG. 2A). The same three pial arteriolar MCA branches were electrically cauterized and dye injections were repeated to ensure the interruption of flow through the cauterized arterioles. The incision was then closed and the animal returned to its cage and allowed free access to food and water. This permanent ischemia model produces a highly reproducible (Forder, 2005) small infarction that is limited to the cortex underlying the coagulated terminal pial arteries (FIG. 2A,B).

Permanent Middle Cerebral Artery Occlusion

The left middle cerebral artery was occluded by the intraluminal suture method described by Longa (1989). In brief, the left common carotid artery (CCA) was exposed through a midline neck incision and was dissected free from surrounding nerves and fascia, from its bifurcation to the base of the skull. The occipital artery branches of the external carotid artery (ECA) were then isolated, and these branches were dissected and coagulated. The ECA was dissected further distally and coagulated along with the terminal lingual and maxillary artery branches, which were then divided. The internal carotid artery (ICA) was isolated and carefully separated from the adjacent vagus nerve, and the pterygopalatine artery was ligated close to its origin. The tip of a 4-cm length of 3-0 monofilament nylon suture (Harvard Apparatus) was rounded by burning to achieve a tip diameter of 0.33-0.36 mm and tip length of 0.5-0.6 mm and coated with poly-L-lysine (Belayev et al., 1996). The suture was introduced through the CCA and advanced into the ICA and thence into the circle of Willis (about 18-20 mm from the carotid bifurcation), effectively occluding the middle cerebral artery. The silk suture around the CCA was tightened around the intraluminal nylon suture to secure it and permanently occlude the middle cerebral artery. Sham operated animals underwent the identical surgical procedure, including permanent ligation of the CCA, but without suture insertion to occlude the MCA. The pMCAO procedure was considered to be adequate if the animal's neurobehavioral score (below) exceeded 10 at 2 h after pMCAO. Animals were allowed to recover from anesthesia at room temperature.

Neurobehavioral Evaluation

Behavioral scoring was performed at 2 h and again at 24 h after pMCAO. The battery consisted of two tests that have been used previously (Aarts, 2002) to evaluate various aspects of neurological function: the postural reflex test (Bederson, 1986b), and the forelimb placing test (De Ryck, 1989). Neurological function was graded on a scale of 0 to 12 (normal score, 0; maximal score, 12).

Infarct Volume Evaluation.

At 24 h after pMCAO the animals were deeply anaesthetized employing halothane inhalation and the brains were quickly removed, sliced into 8 standard coronal sections, and incubated for 30 min in 2% triphenyltetrazolium chloride (TTC; Sigma, St. Louis, USA) in saline at 37° C. This standard technique (Hatfield, 1991; Bederson, 1986a; Joshi, 2004) reveals the infracted area as a pale, unstained portion of the brain section. Each section was digitally photographed, and the infarcts were then traced onto templates representing the 8 standardized coronal slices. The use of the templates corrects for any brain edema produced by the infarct, allowing for a more accurate determination of infarct volume. Each infarct area was then digitally traced from the templates (MOD Version 6.0, Imaging Research Inc., St. Catharines, Ontario, Canada) and the 8 infarct areas per brain were integrated in order to obtain the volume.

Data Analysis

All animal surgery including drug infusions, behavioural assessments and infarct volume determinations were performed by individuals blinded to the treatment group. Exclusions of animals from analysis of the pMCAO data (Results section) were based on pre-established criteria, applied prospectively by individuals blinded to the treatment group. The pre-established exclusion criteria were: all deaths prior to animal sacrifice, failure to maintain CT pre pMCAO and for 10 min post-MCAO at 37.0±1.0° C., failure to maintain $pCO_2$ between 35 and 45 mmHg or mean arterial blood pressure (MABP) above 100 mm Hg during surgery, failure of the neurobehavioral score to exceed 10 at 2 h after pMCAO, technical surgical complications, and the lack of any basal ganglia infarct on morphological evaluation. Data are expressed in mean±S.E.M. Differences between groups were analyzed using ANOVA followed by multiple comparisons using the Bonferroni correction.

RESULTS

Effects of Overnight Fasting on Blood Glucose

The fasting of animals is common practice in experimental stroke studies (e.g., Belayev, 2005b; Aronowski, 2003; Nakashima, 1995; Kuge, 1995), and can be practiced, in large part, due to the adverse impact of hyperglycemia on the efficacy of neuroprotective compounds. To measure the effect of overnight fasting on blood glucose, SD rats were either permitted access to water only (fasting period of 16 hours; n=8; body weight 278.38±14.86 g) or to both food and water overnight (non-fasting; n=12; body weight 276.50 g±13.69 g). Blood glucose was determined in the morning. Animals that were permitted free overnight access to both food and water exhibited significantly higher blood glucose levels than animals that had free overnight access to water, but not food (5.50±0.08 mMol/l vs. 3.71±0.21 mMol/l, respectively; $t_{18}$=9.134; p<0.001).

Effects of PSD-95 Inhibitors on Core Temperature

Previous experience has shown that the neuroprotective effects of some anti-ischemic drugs might have been, at least in part, related to drug-induced hypothermia (e.g., MK-801; Corbett, 1990). Conversely, if a drug induces hyperthermia, its protective effects might be diminished (Noor, 2005; Memezawa, 1995). To determine whether PSD-95 inhibition affected core temperature (CT), it was measured in rats (n=6) implanted with telemetric intra-peritoneal temperature monitors. CTs were measured from 20 h before until 24 h after a single intravenous injection of 3 nMole/g of Tat-NR2B9c$_{(SDV)}$, the highest PSD-95 inhibitor dose used in the present study. Changes in CT were compared to those of animals undergoing sham surgery (Methods) with a saline infusion (vehicle, n=4). Animals in both groups exhibited a mild increase in CT after termination of anesthesia (~0.5° C. increase) which returned to baseline within 10-15 hours. However, there were no differences in CT at any time point between the sham (vehicle) and peptide-infused animals (FIG. 1A,B). Transient elevations in CT have been noted in rodents after general anesthesia (Hansen et al., 2002; Weinandy et al., 2005), and have been attributed to anaesthetic stress.

Effect of pMCAO on Core Temperature.

Spontaneous sustained hyperthermia is a recognized consequence of severe ischemia following MCAO (Roberts-Lewis, 1993; Zhao, 1994; Reglodi, 2000; Legos, 2002; Abraham, 2002, 2003), possibly due to hypothalamic injury (Zhao, 1994), or to early microglial activation in the temperature-regulatory centers of the hypothalamus (Abraham, 2003). To achieve consistent and sustained hyperthermia after pMCAO, the filament used for MCA occlusion was modified according to Abraham, who demonstrated that the degree of post-ischemic hyperthermia and the magnitude of cerebral infarction are related to the size of the occluding filament (Abraham, 2002). pMCAO was induced using a filament with a tip diameter of 0.33-0.36 mm (Methods). This caused the animals' temperature to rise rapidly after pMCAO, peaking at ~39.5° C. approximately 2 h after pMCAO and remaining elevated at or above 39° C. for the duration of the 24 h observation period (FIG. 1D).

It was next determined whether the spontaneous hyperthermia was the result of the animals' sustaining a defect in their ability to thermoregulate. Using a feedback-controlled cage temperature regulator (Methods) induction of normothermia was attempted in the ischemic animals (n=8) by cooling the cage whenever their CT exceeded a threshold of 37.1° C. (FIG. 1E). The animals were compared with a cohort which underwent pMCAO, but whose cage was maintained at room temperature (n=8; FIG. 1D). The hyperthermic response to pMCAO was resistant to cooling by ambient temperature reduction, and the animals maintained a CT≥39° C. even when the cage temperature dropped to ~8° C. (FIG. 1E). Prior studies suggest that blunting this hyperthermic response requires extreme measures, consisting of shaving of large areas of fur, placing the animals at 4° C., and topically applying 70% alcohol (Reglodi, 2000). Thus it was concluded that the robust and sustained hyperthermia after pMCAO was not due to the inability of the animals to thermoregulate but rather, was due to an alteration in the animal's temperature set-point (fever).

Effect of Pial Vessel Occlusion on Core Temperature

As the pMCAO model produced hyperthermia, a permanent ischemia model was sought that would not alter CT so that neuroprotection using PSD-95 inhibitors could be evaluated independently of the hyperthermia produced by pMCAO. To this end a pial vessel occlusion model (Methods) was used that produces a small infarction (FIG. 2A,B) in order to not impact CT. Animals subjected to this ischemic insult (n=5) exhibited no significant changes in CT as compared with sham surgery animals (FIG. 1A,C).

Relationship Between Core and Brain Temperature in pMCAO.

Although brain temperature can be most directly correlated with the extent of ischemic damage (Busto, 1987a, 1987c, 1989b; Dietrich, 1992; Minamisawa, 1990a; Morikawa, 1992), it is unlikely that any systemically-administered drug can affect brain temperature independently of Core temperature. To determine whether core temperature measurements were reflective of brain temperature in this study, some animals that had undergone pMCAO with core temperature monitoring also underwent temperature measurements directly from brain and, in some experiments, from temporalis muscle as a surrogate measure of brain temperature. Core temperature measurements correlated to within 0.5° C. with brain and temporalis muscle temperatures in animals receiving either saline (n=6; FIG. 1F) or 3 nMole/g of Tat-NR2B9c$_{(SDV)}$ (n=6; FIG. 1F). Thus CT measurements were used for the remainder of the study.

Exclusions from Data Analysis.

Exclusion criteria (Methods) were applied by individuals blinded to the treatment groups. All exclusions from the pial vessel occlusion study are detailed in Table 1. No animals were excluded after dosing with the PSD-95 inhibitor. Exclusions from analysis of the two pMCAO studies are listed in Table 2. In brief, perioperative mortalities were the main reasons for excluding animals from analysis. Overall mortality rates were 8.7% and 16.4% for animals in the first and second independent pMCAO studies, respectively, with no apparent relationship to the drug infusions or identities. Necropsies revealed that mortalities were primarily associated with subarachnoid and/or brain hemorrhages induced by arterial perforations by the pMCAO filament.

Effect of PSD-95 Inhibitors on Infarction Volume.

In all experiments, the PSD-95 inhibitors were administered 1 h after the onset ischemia, as treatment after stroke onset likely has the most clinical relevance.

The effects of Tat-NR2B9c$_{(SDV)}$ in the pial vessel occlusion model (FIG. 2A) were first evaluated. The animals were treated with vehicle (saline), low (0.3 nMole/g) or high (3 nMole/g) doses of the PSD-95 inhibitor at 1 h after the vessel occlusion. As a farther control in this screening study, Tat-NR2B9c$_{(ADA)}$ was used, a peptide incapable of binding PSD-95 (Kornau, 1995; Methods), and which does not affect excitotoxic vulnerability (Aarts, 2002; Arundine et al., 2004) or infarct size (Aarts, 2002). Treatment of the animals with either vehicle or Tat-NR2B9c$_{(ADA)}$ resulted in infarcts localized to the cortex underlying the pial vessel occlusion, occupying about 9-10% of the hemisphere volume (FIG. 2B). Treatment of the animals with Tat-NR2B9c$_{(SDV)}$ (3 nMole/g) reduced the infarcts by about 60% (FIG. 2C,D).

Next, the PSD-95 inhibitors in pMCAO was used. All of the animals that underwent pMCAO exhibited hyperthermia to the same degree, with CT exceeding 39.5° C. in the first 8 h, and remaining at about 39° C. thereafter (FIG. 3A-E). Injection of the PSD-95 inhibitors had no impact on the hyperthermic response post pMCAO as there were no significant differences between the treatment groups in either the peak or the mean temperature elevation (ANOVA, p>0.15 for each).

Figure 4:
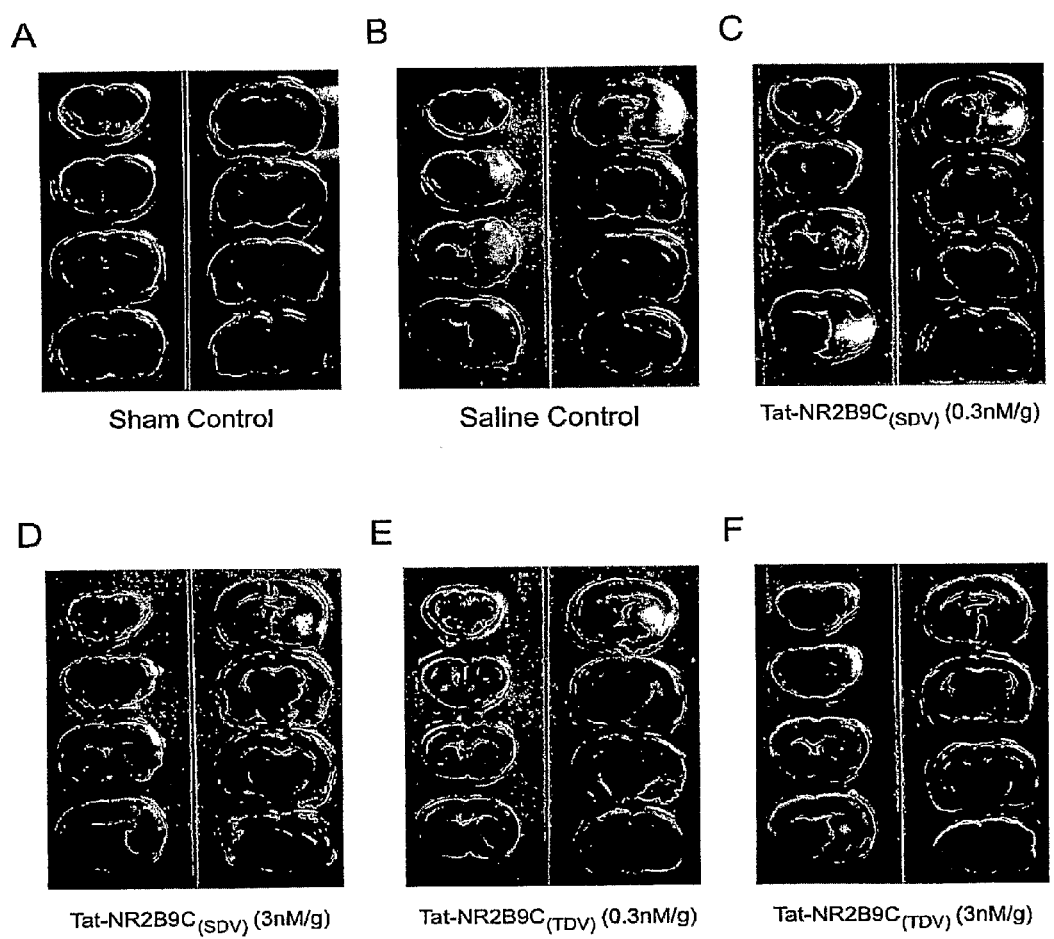
FIG. 4. Representative TTC stained coronal brain sections taken from animals 24 h after subjecting them to sham surgery (A) or pMCAO (B-F). Animals in B-F were treated with the indicated PSD-95 inhibitor at the indicated dose at 1 h after pMCAO.
Figure 5:
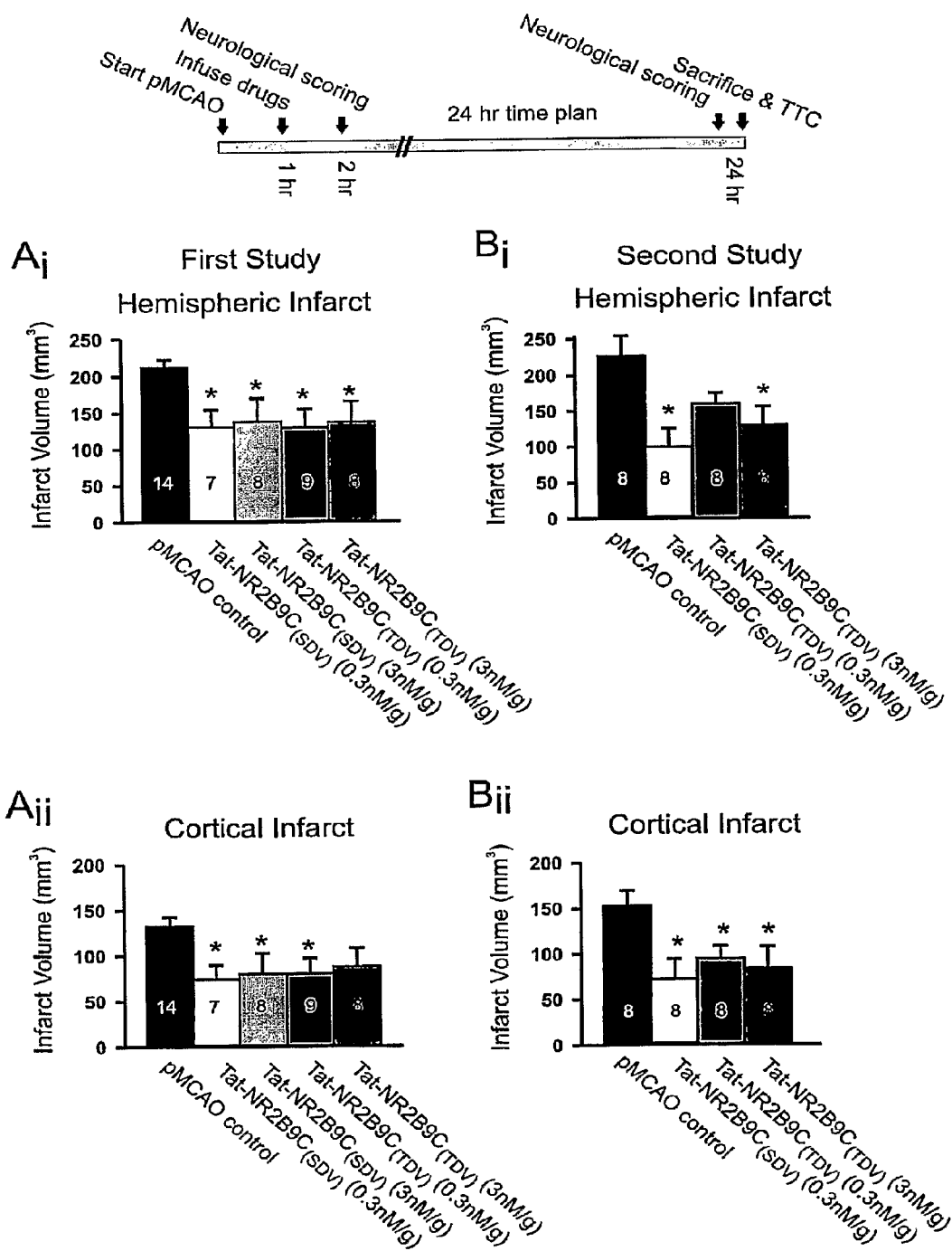
FIG. 5. Reduction of pMCAO infarct volumes by post-treatment with PSD-95 inhibitors. Ai and Aii: Effects of PSD-95 inhibitors on hemispheric (Ai) and cortical (Aii) infarct volumes in the first blinded study. Bi and Bii: Effects of PSD-95 inhibitors on hemispheric (Bi) and cortical (Bii) infarct volumes in the second blinded study. Animals were treated with the PSD-95 inhibitors at the indicated doses at 1 h after pMCAO. Asterisks: significantly different from saline controls (ANOVA followed by multiple comparisons using the Bonferroni correction). Inset: study paradigm. Number of animals per group is provided in Table 2.
Figure 6:
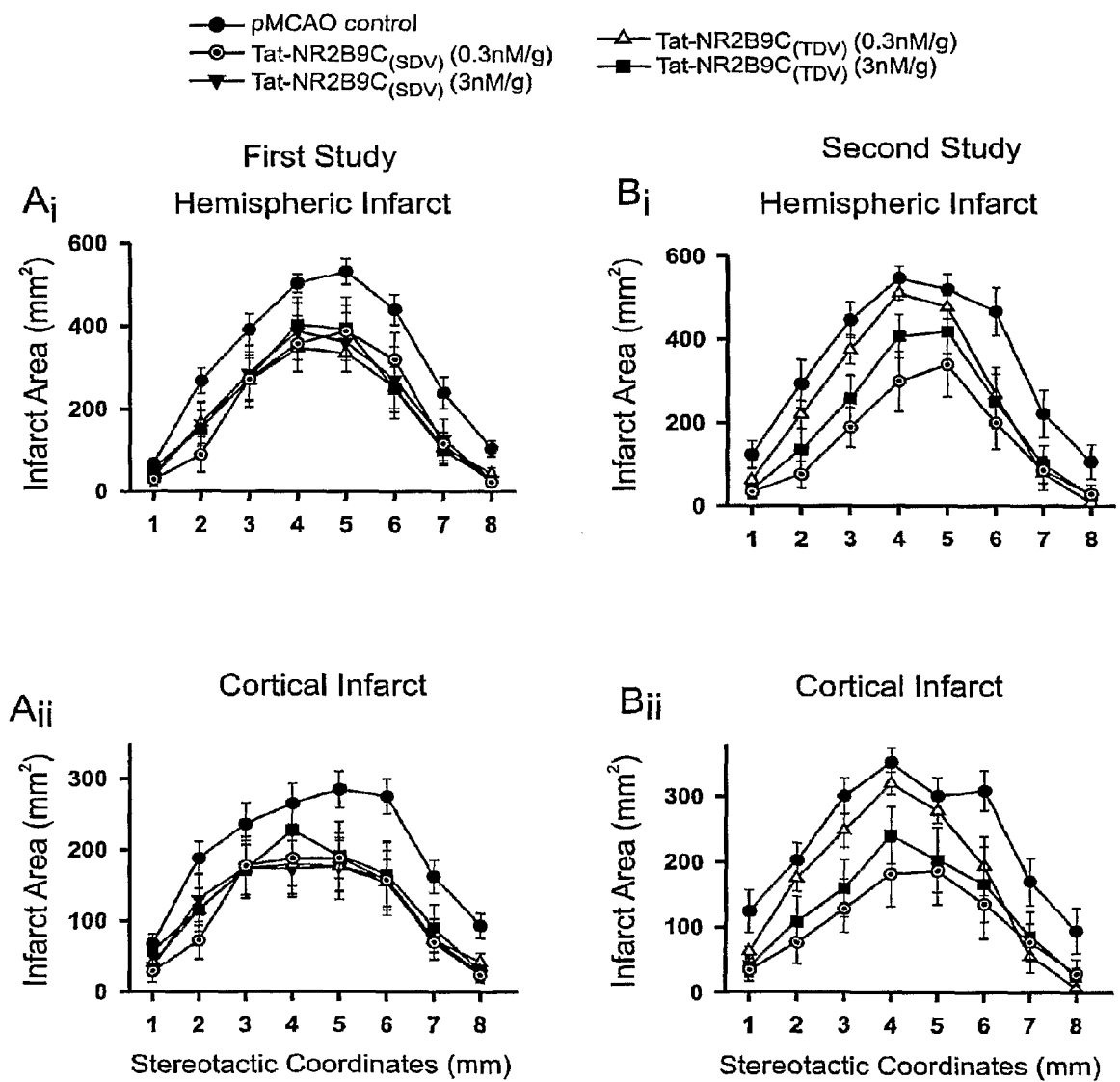
FIG. 6. Infarct areas from 8 coronal brain sections from which the volumes in FIG. 5 were derived. Each symbol indicates the mean±SE area in a given stereotactic plane for the conditions indicated.

Animals that had undergone pMCAO without treatment sustained large hemispheric infarcts that, at 24 h, occupied the majority of the cortical surface and deep structures (FIG. 4B). However, treatment with the PSD-95 inhibitor Tat-NR2B9c$_{(SDV)}$ 1 h after pMCAO (0.3-3.0 nM/g) attenuated the total infarct volume (e.g., FIG. 4C,D) by as much as 40% (FIG. 5A$_i$), with the effects being most pronounced in the cortical component of the infarct (~45% cortical infarct reduction; FIG. 5A$_{ii}$). The reduction in tissue infarction was observable in all sterotactic planes used to quantify the infarct volumes (FIGS. 4C,D. 6A$_i$,A$_{ii}$).

Neuroprotection by the Tat-NR2B9c$_{(SDV)}$ peptide has been reported by us previously in-vitro (Aarts, 2002; Arundine, 2004) and in-vivo using a model of transient, reversible MCAO (Aarts, 2002). The terminal amino acids in the −0 and −2 positions are critical, and mutation of even one residue prevents or reduces the association of the NR2B C-terminus with PSD-95 (Bassand, 1999). However, it is predicted that peptides ending with the C-terminal TDV consensus sequence should also bind similar protein targets, including PSD-95 (Komau, 1995, 1997; Niethammer, 1996; Bassand, 1999). If so, then they can exhibit similar neuroprotective effects, though this has never been determined in any disease model. To test this hypothesis, Tat-NR2B9c$_{(TDV)}$ was used at 0.3 nM/g and at 3.0 nM/g in the same study and under the same conditions as Tat-NR2B9c$_{(SDV)}$. As shown in FIGS. 4E,F, 5A$_i$,A$_{ii}$, and 6A$_i$,A$_{ii}$, this peptide also reduced hemispheric infarction volume by ~35%, and cortical infarction by 40-45%.

Next, the reproducibility of the novel findings arising from the first study was evaluated. A second, confirmatory, study was carried out similarly to the first. The confirmatory study focused on replicating the effects of the lower concentration of the Tat-NR2B9c$_{(SDV)}$ peptide, and the effects of the Tat-NR2B9c$_{(TDV)}$ peptides. As surgical technique is a key variable in animal stroke models, the surgery in the two independent studies was performed by different, blinded, surgeons. As in the first study, all peptides were administered at 1 h after pMCAO. The team conducting the confirmatory study was blinded to the results of the first study.

The confirmatory study yielded similar results to the first, with both the Tat-NR2B9c$_{(SDV)}$ and Tat-NR2B9c$_{(TDV)}$ peptides having had a similar effect on reducing both hemispheric and cortical infarction volumes (FIGS. 5B$_i$,B$_{ii}$, 6B$_i$, B$_{ii}$).

Effect of PSD-95 Inhibitors on Cage Activity and on Neurobehavioral Scores.

Figure 7:
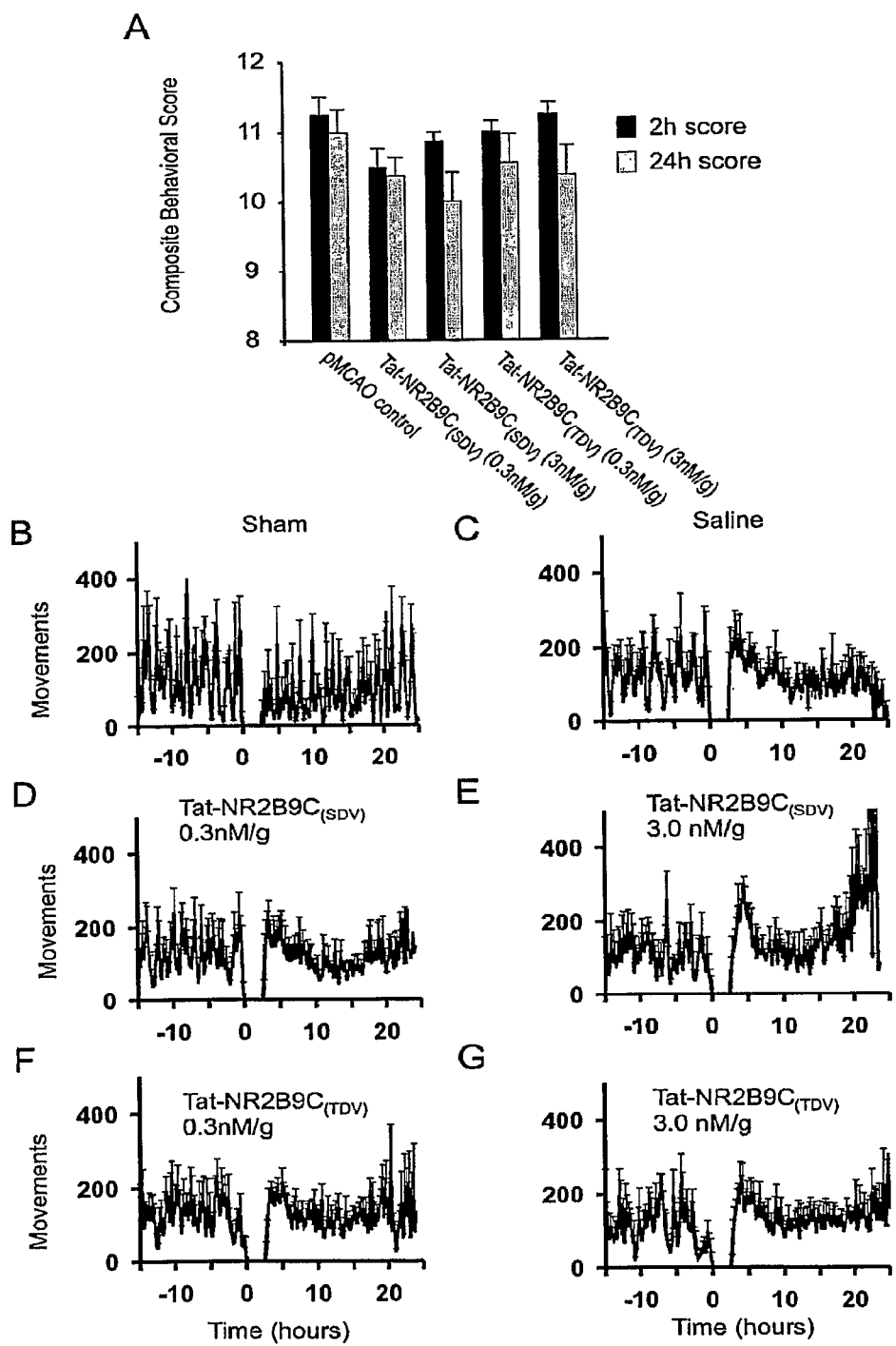
FIG. 7. A. Composite neurobehavioral scores at 2 and 24 hrs after pMCAO for the indicated conditions. B-G: Plots of animal cage activity before and after the permanent MCAO procedure in the different PSD-95 inhibitor groups. Zero indicates time of MCAO.

A disadvantage of the pMCAO intraluminal thread occlusion model combined with hyperthermia and in unfasted animals is that the experimental animals suffer from an extensive brain insult causing severe neurological deficits (composite neurological score >11 in untreated animals; FIG. 7A). Unlike in transient MCAO, in which this score improves spontaneously by 24 h (Belayev, 2001; Aarts, 2002), the untreated animals in this series of experiments remained profoundly impaired (24 h composite neurological scores of ~11). The animals treated with the PSD-95 inhibitors showed a trend towards improved neurological scores 24 h after pMCAO, but these results did not reach statistical significance (paired Student's t-test, P>0.05; FIG. 7A). However, telemetric monitoring of cage activity (Colbourne, 1999; Barber, 2004) revealed that by 24 h animals treated with the PSD-95 inhibitors had similar levels of cage activity as compared with shams (FIG. 7B) and pre-MCAO levels (FIG. 7D-G), whereas the activity in the untreated animals dropped off (FIG. 7C). Longer post-pMCAO recovery times can be necessary to fully evaluate neurological recovery after this profound type of ischemic injury. However, this was not pursued in the present study due to concerns about the longer-term survivability of untreated animals.

BIBLIOGRAPHY

Aarts (2002) Science 298:846-850.
Aarts (2004) Curr Mol Med 4:137-147.
Abraham (2002) Exp Brain Res 142:131-138.
Abraham (2003) Exp Brain Res 153:84-91.
Alvarez-Sabin (2003) Stroke 34:1235-1241.
Aronowski (2003) Stroke 34:1246-1251.
Arundine (2004) J Neurosci 24:8106-8123.
Asoh (2002) Proc Natl Acad Sci USA 99:17107-17112.
Azzimondi (1995) Stroke 26:2040-2043.
Barber (2004) Stroke 35:1720-1725.
Bassand (1999) Eur J Neurosci 11:2031-2043.
Beckman (1996) Chem Res Toxicol 9:836-844.
Beckman (1996) 271:C1424-C1437.
Bederson (1986a) Stroke 17:1304-1308.
Bederson (1986b) Stroke 17:472-476.
Belayev (1996) Stroke 27:1616-1622.
Belayev (2005a) Stroke 36:1071-1076.
Belayev (2001) Stroke 32:553-560.
Belayev (2005b) Stroke 36:326-331.
Borsello (2003) Nat Med 9:1180-6
Boysen (2001) Stroke 32:413-417.
Brenman (1997) Current Opin Neurobiol 7:374-378.
Brenman (1996) Cell 84: 757-767.
Busto (1987a) J Cereb Blood Flow Metab 7:729-738.
Busto (1989a) Neurosci Lett 101:299-304.
Busto (1989b) Stroke 20:1113-1114.
Busto (1987b) Cereb Blood Flow Metab 7:729-738.
Busto (1987c) J Cereb Blood Flow Metab 7:729-738.
Cao (2002) J Neurosci 22:5423-5431.
Chen (1991) Neurology 41:1133-1135.
Chen (1993) J Cereb Blood Flow Metab 13:389-394.
Colbourne (1999) J Cereb Blood Flow Metab 19:742-749.
Corbett (1990) Brain Res 514:300-304.
Crow (1996) Adv Exp Med Biol 387:147-161.
Davis (1997) Lancet 349:32.
Davis (2000) Stroke 31:347-354.
Dawson (1993) J Neurosci 13:2651-2661.
Dawson (1991) Proc Natl Acad Sci USA 88:6368-6371.
De Keyser (1999) Trends Neurosci 22:535-540.
De Ryck (1989) Stroke 20:1383-1390.
Denicourt (2003) Trends Pharmacol Sci 24:216-218.
Dietrich (1992) J Neurotrauma 9:Suppl 2:S475-85.
Dietz (2002) Mol Cell Neurosci 21:29-37.
Dirnagl (1999) Trends Neurosci 22:391-397.
Donnan (2005) Stroke 36:2326.
Elsersy (2004) Anesthesiology 100:1160-1166.
Eum (2004) Free Radic Biol Med 37:1656-1669.
Farrokhnia (2005) Acta Neurol Scand 112:81-87.
Fisher (2005) Stroke 36:2324-2325.
Forder (2005) Am J Physiol Heart Circ Physiol 288:H1989-H1996.
Ginsberg (1998) Stroke 29:529-534.
Ginsberg (1992) Cerebrovasc Brain Metab Rev 4:189-225.
Gladstone (2002) Stroke 33:2123-2136.
Hansen (2002) Lab Anim 36:144-152.
Hatfield (1991) Neuropathol Appl Neurobiol 17:61-67.
Horiguchi (2003) Stroke 34:1015-1020.
Hung (2002) J Biol Chem 277:5699-5702.
Ikonomidou (2000) Proc Natl Acad Sci USA 97:12885-12890.
Ikonomidou (2002) Lancet Neurology 383-386.
Joshi (2004) Brain Res Brain Res Protoc 13:11-17.
Kaste (2005) Stroke 36:2323-2324.
Kilic (2002) Ann Neurol 52:617-622.
Kilic (2003) Stroke 34:1304-1310.
Kim (2005) Mol Cells 19:88-96.
Komau (1995) Science 269:1737-1740.
Komau (1997) Current Opin Neurobiol 7:368-373.
Kuge (1995) Stroke 26:1655-1657.
Lees (2000) Lancet 355:1949-1954.
Legos (2002) J Neurosci Methods 113:159-166.
Li (2001) 21:568-576.
Li (2000) Stroke 31:183-192.
Li (1997) Acta Physiol Scand 161:567-580.
Li (1998) Brain Res 782:175-183.
Longa (1989) Stroke 20:84-91.
Memezawa (1995) Brain Res 670:48-52.
Migaud (1998) Nature 396:433-439.
Minamisawa (1990a) Stroke 21:758-764.
Minamisawa (1990b) J Cereb Blood Flow Metab 10:365-374.
Minamisawa (1990c) TAnn Neurol 28:26-33.
Morikawa (1992) J Cereb Blood Flow Metab 12:380-389.
Morris (1999) J Neurosurg 91:737-743.
Nakashima (1995) Anesthesiology 82:1199-1208.
Niethammer (1996) J Neurosci 16:2157-2163.
Noor (2005) Stroke 36:665-669.
Paolino (2005) J Neurosci Nurs 37:130-135.
Reglodi (2000) Exp Neurol 163:399-407.
Reith (1996) Lancet 347:422-425.
Roberts-Lewis (1993) J Neurochem 61:378-381.
Rothman (1995) Trends Neurosci 18:57-58.
Rothman (1987) Trends Neurosci 10:299-302.
Sattler (1999) Science 284:1845-1848.
Schwarze (1999) Science 285:1569-1572.
Sheng (2001) Proc Natl Acad Sci USA 98:7058-7061.
STAIR Committee (1999) Stroke 30:2752-2758.
Walters (2005) Cerebrovasc Dis 20:304-309.
Weinandy (2005) Lab Anim 39:200-208.
Ye (1996) Methods Enzymol 269:201-209.
Zhang (1994) Science 263:687-689.
Zhao (1994) Brain Res 649:253-259.

All publications and patents cited in this specification are incorporated by reference as if each individual publication or patent were specifically and individually indicated to be incorporated by reference. Further, any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

Although the present invention has been described with reference to the specific embodiments thereof various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

TABLE 1

Mortalities and Exclusions from Pial Vessel Occlusion Study:

| Group | Animals entered | Surgical Deaths* | Post-op Deaths | Surgical Technique** | Number analyzed |
|---|---|---|---|---|---|
| SALINE | 9 | 2 | 0 | 1 | 6 |
| Tat-NR2B9c$_{(SDV)}$ (0.3 nMole/g) | 9 | 1 | 0 | 1 | 7 |
| Tat-NR2B9c$_{(SDV)}$ (3.0 nMole/g) | 9 | 0 | 0 | 2 | 7 |

Animals excluded due to surgical deaths* or due to difficulties with surgical technique** (difficulty obtaining clean pial cauterization) were all excluded before the drug infusion. There were no exclusions after dosing.

TABLE 2

Mortalities and Exclusions from pMCAO Study
Surgeon # (1/2)

| Group | Animals entered | Surgical Deaths | Post-op Deaths** | excluded because 2 h Neuro-score <=10 | MABP <100 mmHg during surgery | pCO$_2$ <35 or >45 | CT <36 or >38° C. pre and 10 min after pMCAO | No basal ganglia infarcts | Number analyzed |
|---|---|---|---|---|---|---|---|---|---|
| SALINE | 19/11 | 1*/0 | 2/3*** | 0/0 | 0/0 | 0/0 | 0/0 | 2/0 | 14/8 |
| Tat-NR2B9c$_{(SDV)}$ (0.3 nMole/g) | 10/9 | 0/0 | 1/1 | 0/0 | 1/0 | 0/0 | 0/0 | 1/0 | 7/8 |
| Tat-NR2B9c$_{(SDV)}$ (3.0 nMole/g) | 9 | 0 | 1 | 0 | 0 | 0 | 0 | 0 | 8 |
| Tat-NR2B9c$_{(TDV)}$ (0.3 nMole/g) | 9/10 | 0/0 | 0/2 | 0/0 | 0/0 | 0/0 | 0/0 | 0/0 | 9/8 |
| Tat-NR2B9c$_{(TDV)}$ (3.0 nMole/g) | 10/11 | 0/0 | 0/3 | 0/0 | 2/0 | 0/0 | 0/0 | 0/0 | 8/8 |
| Sham Surgery | 4 | 0 | 0 | 0 | 0 | 0 | 0 | 0 | 4 |
| pMCAO with feedback Cooling | 8 | 0 | 0 | 0 | 0 | 0 | 0 | 0 | 8 |

The two numbers in each cell (X/Y) represent animal numbers for surgeons from pMCAO study #1 and #2, respectively.
*Expired before MCAO, during arterial catheterisation
**Necropsy revealed brain/subarachnoid hemorrhage likely incurred from MCAO filament insertion.
***One animal euthanized due to respiratory problems 5 h post pMCAO surgery.
Necropsy revealed tracheal injury related to intubation.

TABLE 3-1

Physiological Parameters of All Groups from 1$^{st}$ Study.

| Groups | Control | SDV 0.3 nmol/g | SDV 3 nmol/g | TDV 0.3 nmol/g | TDV 3 nmol/g | Sham |
|---|---|---|---|---|---|---|
| N | 8 | 8 | 8 | 9 | 8 | 4 |
| BW (g) | 275.25 ± 7.83 | 291.13 ± 4.30 | 302.87 ± 8.22 | 296.44 ± 5.15 | 300.75 ± 4.67 | 291.25 ± 4.05 |
| 24 hrs | 248.75 ± 8.04 | 250.00 ± 3.55 | 242.80 ± 4.12 | 254.63 ± 2.73 | 259.38 ± 4.86 | 277.25 ± 4.71 |
| NS@2 hrs | 11.25 ± 0.25 | 10.50 ± 0.27 | 10.88 ± 0.13 | 11.00 ± 0.00 | 11.25 ± 0.16 | 0 |
| 24 hrs | 11.00 ± 0.33 | 10.37 ± 0.26 | 10.00 ± 0.42 | 10.55 ± 0.41 | 10.37 ± 0.42 | 0 |
| MABP (mmHg) | 126.13 ± 5.80 | 119.63 ± 5.14 | 126.75 ± 4.39 | 126.00 ± 5.54 | 123.63 ± 6.27 | 108.75 ± 3.88 |
| 10 min | 139.38 ± 4.88 | 136.75 ± 4.85 | 134.38 ± 7.42 | 121.44 ± 5.23 | 140.63 ± 7.64 | 132.25 ± 8.44 |
| 70 min | 134.88 ± 3.60 | 139.38 ± 5.14 | 103.38 ± 5.06 | 129.44 ± 6.54 | 102.13 ± 2.39 | 120.75 ± 5.59 |
| pH | 7.43 ± 0.01 | 7.42 ± 0.01 | 7.44 ± 0.01 | 7.42 ± 0.02 | 7.44 ± 0.01 | 7.43 ± 0.01 |
| 10 min | 7.42 ± 0.01 | 7.42 ± 0.01 | 7.43 ± 0.01 | 7.42 ± 0.01 | 7.43 ± 0.01 | 7.43 ± 0.01 |
| 70 min | 7.41 ± 0.01 | 7.43 ± 0.01 | 7.41 ± 0.01 | 7.41 ± 0.01 | 7.40 ± 0.01 | 7.42 ± 0.01 |
| pCO$_2$ (mmHg) | 38.5 ± 1.27 | 37.5 ± 0.42 | 37.38 ± 0.78 | 38.11 ± 0.81 | 39.75 ± 0.70 | 39.25 ± 0.63 |
| 10 min | 40.00 ± 0.91 | 41.38 ± 0.98 | 40.75 ± 1.03 | 39.33 ± 0.73 | 40.25 ± 0.99 | 38.25 ± 0.25 |
| 70 min | 39.88 ± 1.13 | 39.00 ± 1.35 | 37.00 ± 0.53 | 38.67 ± 0.93 | 40.38 ± 0.84 | 38.50 ± 1.50 |

TABLE 3-1-continued

Physiological Parameters of All Groups from 1st Study.

| Groups | Control | SDV 0.3 nmol/g | SDV 3 nmol/g | TDV 0.3 nmol/g | TDV 3 nmol/g | Sham |
|---|---|---|---|---|---|---|
| pO$_2$ (mmHg) | 142.13 ± 4.80 | 137.75 ± 7.18 | 130.63 ± 5.63 | 131.44 ± 9.11 | 130.63 ± 6.24 | 130.25 ± 15.39 |
| 10 min | 140.00 ± 5.83 | 132.38 ± 6.77 | 129.75 ± 4.67 | 124.22 ± 6.34 | 136.00 ± 2.57 | 122.00 ± 5.67 |
| 70 min | 136.38 ± 4.93 | 139.38 ± 7.15 | 136.13 ± 5.28 | 137.67 ± 4.75 | 132.25 ± 4.65 | 125.5 ± 8.58 |

BW—body weight;
NS—neurobehavior score.
Mean ± SEM

TABLE 3-2

Physiological Parameters of All Groups from 2nd Study.

| Groups | Control | SDV 0.3 nmol/g | TDV 0.3 nmol/g | TDV 3 nmol/g |
|---|---|---|---|---|
| N | 8 | 8 | 8 | 8 |
| BW (g) | 293.75 ± 4.07 | 287.75 ± 6.84 | 293.50 ± 2.28 | 296.25 ± 3.25 |
| NS@2 hrs | 10.75 ± 0.16 | 10.86 ± 0.13 | 10.63 ± 0.18 | 10.60 ± 0.24 |
| 24 hrs | 10.88 ± 0.13 | 10.43 ± 0.28 | 10.63 ± 0.18 | 11.00 ± 0.00 |
| MABP (mmHg) | 116.00 ± 5.29 | 114.50 ± 3.76 | 119.00 ± 4.11 | 124.13 ± 6.29 |
| 10 min | 134.00 ± 8.76 | 134.38 ± 4.16 | 140.50 ± 4.69 | 146.63 ± 4012 |
| 70 min | 137.25 ± 5.52 | 125.75 ± 4.94 | 129.25 ± 8.09 | 130.25 ± 12.26 |
| pH | 7.39 ± 0.01 | 7.39 ± 0.01 | 7.38 ± 0.02 | 7.41 ± 0.01 |
| 10 min | 7.40 ± 0.01 | 7.41 ± 0.01 | 7.38 ± 0.01 | 7.38 ± 0.02 |
| 70 min | 7.39 ± 0.01 | 7.41 ± 0.02 | 7.41 ± 0.01 | 7.39 ± 0.02 |
| pCO$_2$ (mmHg) | 40.13 ± 1.19 | 39.13 ± 1.25 | 39.25 ± 1.06 | 38.63 ± 1.05 |
| 10 min | 40.88 ± 0.93 | 38.63 ± 0.89 | 42.75 ± 0.59 | 37.50 ± 0.80 |
| 70 min | 39.13 ± 1.25 | 39.50 ± 1.22 | 41.75 ± 1.13 | 40.88 ± 1.42 |
| pO$_2$ (mmHg) | 119.13 ± 7.83 | 142.75 ± 4.34 | 133.13 ± 5.15 | 141.13 ± 10.44 |
| 10 min | 121.25 ± 6.09 | 137.75 ± 5.55 | 132.00 ± 4.92 | 120.13 ± 6.53 |
| 70 min | 120.50 ± 3.01 | 126.38 ± 4.79 | 121.00 ± 4.39 | 124.63 ± 4.44 |

---

What is claimed is:

1. A method for reducing the damaging effect of stroke in a patient having stroke or traumatic injury to the CNS exacerbated by fever comprising administering to the patient an effective amount of a peptide having an amino acid sequence comprising ESDV (SEQ ID NO:3) or ETDV (SEQ ID NO:5), wherein the peptide is linked to an internalization peptide or derivatized to improve the ability of the peptide to be cross a membrane, and thereby reducing the damaging effect of the stroke or traumatic injury to the CNS, wherein the patient has a fever of at least 39° C. on initiating treatment.

2. The method of claim 1, wherein a peptide having an amino acid sequence comprising KLSSIETDV (SEQ ID NO:10) is administered.

3. The method of claim 2, wherein a peptide having an amino acid sequence comprising YGRKKRRQRRRKLSSIETDV (SEQ ID NO:11) is administered.

4. The method of claim 2, wherein a peptide having an amino acid sequence consisting of YGRKKRRQRRRKLSSIETDV (SEQ ID NO:11) is administered.

5. The method of claim 1, wherein a peptide having an amino acid sequence comprising KLSSIESDV (SEQ ID NO:9) is administered.

6. The method of claim 1, wherein a peptide having an amino acid sequence comprising YGRKKRRQRRRKLSSIESDV (SEQ ID NO:12) is administered.

7. The method of claim 6, wherein a peptide having an amino acid sequence consisting of YGRKKRRQRRRKLSSIESDV (SEQ ID NO:12) is administered.

8. The method of claim 1, wherein the patient has stroke exacerbated by a fever of at least 40° C. at least for a period between 6-24 hours after onset of stroke.

9. The method of claim 1, wherein the fever is due to concurrent infection.

10. The method of claim 1, wherein the fever is due to location of the stroke in a region of the brain affecting body temperature regulation or set-point.

11. The method of claim 1, wherein the subject is suffering from hyperglycemia due to diabetes substantially concurrent with onset of stroke.

12. The method of claim 1, wherein the stroke is an ischemic stroke.

13. The method of claim 1, wherein the method reduces the infarction volume resulting from the stroke by at least 15%.

14. The method of claim 1, wherein the medicament is in unit dosage form and contains from 0.05 to 500 mg, optionally 0.1 to 100 mg, 0.5 to 50 mg, or 1-20 mg of the peptide.

15. The method of claim 1, wherein the administering is before onset of the stroke or other traumatic injury to the CNS.

16. The method of claim 1, wherein the administering is after onset of the stroke or other traumatic injury to the CNS.

* * * * *

UNITED STATES PATENT AND TRADEMARK OFFICE
CERTIFICATE OF CORRECTION

PATENT NO.       : 8,685,925 B2
APPLICATION NO. : 12/307581
DATED            : April 1, 2014
INVENTOR(S)      : Michael Tymianski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1301 days.

Signed and Sealed this
Thirtieth Day of May, 2017

Michelle K. Lee
*Director of the United States Patent and Trademark Office*